US009777258B2

(12) United States Patent
Sancho-Bru et al.

(10) Patent No.: US 9,777,258 B2
(45) Date of Patent: *Oct. 3, 2017

(54) METHODS FOR DIFFERENTIATING CELLS INTO HEPATIC STELLATE CELLS AND HEPATIC SINUSOIDAL ENDOTHELIAL CELLS, CELLS PRODUCED BY THE METHOD, AND METHODS FOR USING THE CELLS

(71) Applicant: Katholieke Universiteit Leuven, Leuven (BE)

(72) Inventors: Pau Sancho-Bru, Barcelona (ES); Catherine M. Verfaillie, Leuven (BE)

(73) Assignee: Katholieke Universiteit Leuven (BE)

( * ) Notice: Subject to any disclaimer, the term of this patent is extended or adjusted under 35 U.S.C. 154(b) by 0 days.

This patent is subject to a terminal disclaimer.

(21) Appl. No.: 14/750,358

(22) Filed: Jun. 25, 2015

(65) Prior Publication Data
US 2016/0145570 A1 May 26, 2016

Related U.S. Application Data

(62) Division of application No. 13/162,228, filed on Jun. 16, 2011, now Pat. No. 9,090,878.
(Continued)

(51) Int. Cl.
*C12N 5/071* (2010.01)
(52) U.S. Cl.
CPC ........ *C12N 5/067* (2013.01); *C12N 2501/113* (2013.01); *C12N 2501/115* (2013.01); *C12N 2501/119* (2013.01); *C12N 2501/12* (2013.01); *C12N 2501/155* (2013.01); *C12N 2501/16* (2013.01); *C12N 2501/40* (2013.01); *C12N 2501/415* (2013.01); *C12N 2506/02* (2013.01); *C12N 2506/45* (2013.01)

(58) Field of Classification Search
CPC . C12N 5/067; C12N 2506/03; C12N 2506/45
See application file for complete search history.

(56) References Cited

U.S. PATENT DOCUMENTS

| 5,486,359 A | 1/1996 | Caplan et al. |
| 5,827,735 A | 10/1998 | Young et al. |

(Continued)

FOREIGN PATENT DOCUMENTS

| WO | WO 96/23870 | 8/1996 |
| WO | WO 99/16863 | 4/1999 |

(Continued)

OTHER PUBLICATIONS

Cambrex specimens, "Polietics Human Mesenchmymal Stem Cell Systems," Cambrex BioScience Walkersville, Inc. (2005).
(Continued)

*Primary Examiner* — Kara Johnson
(74) *Attorney, Agent, or Firm* — Tarolli, Sundheim, Covell & Tummino LLP

(57) ABSTRACT

The invention is directed to methods for culturing cells so that the cells are induced to differentiate into cells that express a hepatic stellate phenotype and cells that express a hepatic sinusoidal endothelial phenotype. The invention is also directed to cells produced by the methods of the invention. The cells are useful, among other things, for treatment of liver deficiency, liver metabolism studies, and liver toxicity studies.

10 Claims, 14 Drawing Sheets

Related U.S. Application Data

(60) Provisional application No. 61/384,175, filed on Jul. 14, 2010, provisional application No. 61/355,909, filed on Jun. 17, 2010.

(56) References Cited

U.S. PATENT DOCUMENTS

| | | | |
|---|---|---|---|
| 5,906,934 | A | 5/1999 | Grande et al. |
| 6,090,625 | A | 7/2000 | Abuljadayel |
| 6,214,369 | B1 | 4/2001 | Grande et al. |
| 6,653,134 | B2 | 11/2003 | Prockop et al. |
| 6,777,231 | B1 | 8/2004 | Katz et al. |
| 7,045,148 | B2 | 5/2006 | Hariri |
| 7,056,738 | B2 | 6/2006 | Prockop et al. |
| 7,229,827 | B2 | 6/2007 | Kim et al. |
| 7,311,905 | B2 | 12/2007 | Hariri |
| 2001/0033834 | A1 | 10/2001 | Wilkison et al. |
| 2001/0046489 | A1 | 11/2001 | Habener et al. |
| 2002/0061587 | A1 | 5/2002 | Anversa |
| 2002/0164794 | A1 | 11/2002 | Wernet |
| 2003/0003090 | A1 | 1/2003 | Prockop et al. |
| 2003/0032179 | A1 | 2/2003 | Hariri |
| 2003/0059414 | A1 | 3/2003 | Ho et al. |
| 2004/0033214 | A1 | 2/2004 | Young et al. |
| 2004/0235165 | A1 | 11/2004 | Prockop et al. |
| 2005/0152995 | A1 | 7/2005 | Chen |
| 2005/0169896 | A1 | 8/2005 | Li et al. |
| 2005/0255588 | A1 | 11/2005 | Young et al. |
| 2006/0177925 | A1 | 8/2006 | Rosenberg et al. |
| 2006/0286544 | A1 | 12/2006 | Mandal et al. |
| 2007/0010484 | A1 | 1/2007 | Schwartz |
| 2007/0104697 | A1 | 5/2007 | Wilkison |
| 2008/0181865 | A1 | 7/2008 | Schaebitz |
| 2008/0248567 | A1 | 10/2008 | Singla |
| 2010/0239542 | A1 | 9/2010 | Young et al. |
| 2010/0239543 | A1 | 9/2010 | Young et al. |
| 2011/0064701 | A1 | 3/2011 | Young et al. |

FOREIGN PATENT DOCUMENTS

| | | |
|---|---|---|
| WO | WO 99/35243 | 7/1999 |
| WO | WO 01/04268 | 1/2001 |
| WO | WO 01/06691 | 2/2001 |
| WO | WO 01/21766 | 3/2001 |
| WO | WO 01/21767 | 3/2001 |
| WO | WO 02/08388 | 3/2001 |
| WO | WO 01/62901 | 8/2001 |
| WO | WO 02/34890 | 5/2002 |
| WO | WO 2004/087896 | 10/2004 |
| WO | 2010049752 A1 | 5/2010 |

OTHER PUBLICATIONS

Prockop, D., "Marrow airomal cells as stem cells for nonhematopoietic tissues" Science; 276:71-74 (1997).
Bjornson et al., "Turning brain into blood: a hemotopoletic fate adopted by adult natural stem cells in vivo" Science; 283:534-537 (1999).
Reyes et al., "Purification and ex vivo expansion of postnatal human marrow masodermal progenitor cells" Blood; 98:2615-25 (2001).
Bouwens, L., "Transdifferentiation versus stem cell hypothesis for the regeneration of islet beta-cells in the pancreas" Microscopy Research and Technique: 43:332-336 (1998).
Reyes et al., "Origin of endothelial progenitors in human postnatel bone marrow" J. Clin. Invest.; 109:1-10 (2002).
Reyes et al., "Characterization of multilineage mesodermal progenitor cells in adult marrow" Abstract No. 124, American Society for Hematology (2001).
Reyes et al., "Turning marrow into brain: generation of gilal and neuronal cells from adult bone marrow mesenchymal stem cells" Abstract No. 1578, American Society for Hematology (2001).
Reyes et al., "Skeletal smooth ad cardiac mescle differentiation from single adult marrow derived mesodermal progenitor cells" Abstract No. 2810, American Society for Hematology (2001).
Reyes et al., "In vitro and in vivo characterization of neural cells derivied from mesenchymal stem cells" Abstract 2128, American Society for Hematology (2001).
Reyes et el., "Endothermal cells generated from human marrow derived mesenchymal stem cells (MSC)" Abstract No. 2276, American Society for Hematology (2001).
Zhao et al., "Immunohistochemical identification of multipotent adult progenitor cells from human bone marrow after transplantation into the rat brain" Brain Res Brain Res Protoc; 11:38-45 (2003).
Jiang et al., "Multipotent progenitor cells can be isolated from postnatal murine bone marrow, muscle, and brain" Exp. Hematol.; 30:898-904 (2002).
Jiang et al., "Pluripotency of mesenchymal stem cells derivied from adult marrow" Nature; 418:41-49 (2002).
Schwartz, R., "Multipotent adult progenitor cells from bone marrow differentiate into hepatocyte-like cells" J Clin Invest.: 108:1291-1302 (2002).
Zhao et al., "Human bone marrow stem cells exhibit neural phenotypes and ameliorate neurological deficits after grafting into the ischemic brain of rats" Exp Neurol; 174:11-20 (2002).
Lamming et al., "Spontaneous circulation of myeloid-lymphoid-initiating cells and SCID-repopulating cells in sickle cell crisis" J. Clin. Invest.; 111:811-819 (2003).
Qi et al., "Identification of genes responsible for osteoblast differentiation from human mesodermal progenitor cells" Nat. Acad. Sci. USA; 100:3305-3310 (2003).
Verfaillie, C. "Investigator Profile" Journal of Hematotherapy and Stem Cell Research; 11:441-448 (2002).
Verfaillie et al., "Stem cells: hype and reality" Hematology (Am Soc Hematol Educ Program): 389-391 (2002).
Verfaille, C., "Optimizing hematopoietic stem cell engraftment: a novel role for thrombopoeltin" J. Clin. Invest.; 110:303-304 (2002).
Liu et al., "Myeloid-lymphoid-initiating cells (ML-1C) are highly enriched in the rhodamine-C-Kit(+) CD33(−)CD38(−) fraction of unbilical cord DC34(+)" Exp. Hematol.; 30:562-569 (2002).
Lewis et al., "Multi-lineage expension potential of primative hematopoietic progenitors: superlority of umbilical cord blood compared to mobilized peripheral blood" Exp. Hematol.; 28:1087-1095 (2002).
Verfaillie, C.M., "Meeting Report on an NHLBI Workshop on ex vivo expansion of stem cells. Jul. 29, 1999, Washington D.C. National Heart Lung and Blood Institute" Exp. Hematol.; 28:361-384 (2000).
Punzel et al., "The myeloid-lymphoid initiating cell (ML-IC) assay assesses the fate of multipotent human progenitors in vitro" Blood; 93:3750-3756 (1999).
Roy et al., "Expression and function of cell adhesion molecules on fatal liver, cord blood and bone marrow hematopoietic progenitors implications for anatomical localization and developmental stage specific regulation of hematopotesis" Exp. Hematol.; 27:302-312 (1999).
Miller et al., "Ex vivo culture of CD34+/Lin−/DR− cells in stroma-derived soluble factors, interleukin-3, and macrophage Inflammatory protein-1 alpha maintains not only myeloid but also lymphoid progenitors in a novel switch culture assay" Blood; 15:4518-4522 (1998).
Verfaillie, C., "Stem cells in chronic myelogenous Leukemia" Hematol. Oncol. Clin. North Am.; 11:1079-1114 (1997).
Prosper et al., "Phenotype and functional characterization of long-term culture-initating cells present in peripheral blood progenitor collections of normal donors heated with granulocyte colony-stimulating factor" Blood; 15:2033-2042 (1998).
Lodie et al., "Systematic analysis of reportedly distinct populations of multipotent bone marrow-derived stem cells reveals a lack of distinction" Tissue Engineering; 8:739-751 (2002).
Pagen Westphal, S., "Adult bone marrow eyed as source of stem cells" Boston Globe, Jan. 24, 2002.
Pagen Westphal, S., "Ultimate stem cell discovered" New Scientist, Jan. 23, 2002.
Wade et al., "Scientist herald a versatile adult cell" The New York Times on the Web, Jan. 25, 2002.

(56) References Cited

OTHER PUBLICATIONS

Rosford et al., "The octamer motif present in the Rex-1 promoter binds Oct-1 and Oct-3 expressed by EC cells and ES cells" Biochem. Biophys. Res. Comm.; 203:1785-1802 (1994).
Rosner et al., "Oct-3 is a maternal factor required for the first mouse embryonic division" Cell; 64:1103-1110 (1991).
Pittenger et al., "Multilineage potential of adult human mesenchymal stem cells"; Science; 284:143-147 (1999).
Ben-Shushan et al., "Rex1, a gene encoding a transcription factor expressed in the early embryo, is reguisted via Oct-3/4 and Oct-8 binding to octamer alta and a novel protein, R ox-1, binding to an adjacent site" Mol. Cell Biol.; 16:1666-1878 (1998).
Reyes et al., "Characterization of multipotent adult progenitor cells, a subpopulation of mesenchymal stem cells" Annals of the New York Academy of Science; 938:231-235 (2001).
Anjos-Afonso and Ronnet, "Nonhematopoietic/endothelial SSE-1+ cells define the most primative progenitors in the adult murine bone marrow mesanohymal compartment" Blood; 109:1296-1305 (2007).
Bertani et al., "Neurogenic potential of human mesenchymal stem cells revisited: analysis by Immunostaining, time-lapse video and microarray" J Cell Sci; 118:3925-36 (2005).
Bodnar et al., "Extension of the life-span by introduction of telomanase into normal human cells" Science: 279:349-382 (1998).
Horwitz et al., "Clarification of the nomenclature for MSC: the international society for cellular therapy position paper" Cytotherapy: 7:393-395 (2005).
Lu et al., "Induction of bone marrow stromal cells to neurons: differentiation, transdifferentiation, or artifact" J Neurosci Res; 77:174-91 (2004).
Neuhuber et al., "Reservation of in vitro differentiation protocols for bone marrow artomal cells: disruption of actin cytoskeleton induces rapid morphological changes and mimics neuronal phenotype" J Neurosci Res; 77:192-204 (2004).
Simonsen et al., "Taiomerase expression extracts the proliferative life-span and maintains the osteogenic potential of human bone marrow stromal cells" Nature Biotechnology; 20:592-696 (2002).
Zimmerman et al., "Lack of taiomatase activity in human mesenchymal stem cells" Leukemia; 17:1146-1148 (2003).
Izadpanah et al., "Biologic properties of masenchymal stem cells derived from bone marrow and adipose tissue" Journal of Cellular Biochemistry; 99:1285-1297 (2006).
Long et al., "Neural cell differentiation in vitro from adult human bone marrow mesenchymal stem cells" Stem Cells and Development; 14:65-69 (2005).
Morisoot et al.,"Human bone marrow mesenchymal stem cell can express insulin and kep transcription factors of the endocrine pancreas development pathway upon genetic and/or microenvironmental manipulation in vitro" Stem Cells; 23:594-604 (2005).
Sanchez-Ramos et al., "Adult bone m arrow stromal cells differentiate into neural cells in vitro" Exp. Neurol.; 164:247-56 (2000).
Eglitis et al., "Hematopoietic cells differentiate into both microgila and macrogila in the brain of adult mice" Proc. Natl. Acad. Sci. USA; 94:4080-85 (1997).
Kopen et al., "Marrow stromal cells migrate throughout forebrain and cerebellum, and they differentiate into estrocytes after injection into neonatal mouse brains" Proc. Natl. Acad. Sci. USA; 98:10711-16 (1999).
Lagasse et al., "Purified hematopoietic stem cells can differniate into heptocytes in vivo" Nature Medicine; 6:1229-1234 (2000).
Wang, X. et al., "Cell fusion is the principal source of bone-marrow-derived hepatocytes" Nature; 422:897-901 (2003).
Giles, J., "The trouble with replication" Nature, 422:344-347 (2006).
Verfaille, C.M., Multipotent adult progenitor cells: an update: Novartis Found Symp., 254:65-65 (2005).
Aldhous et al., "Fresh questions on stem cell findings" New Scientist, Mar. 21, 2007.

Brazelton et al., "From marrow to brain: expression of neuronal phanotypes in adult mice" Science: 290:1775-9 (2000).
Clarke et al., "Generalized potential of adult neural stem cells" Science: 288: 1660-3 (2000).
Johansson et al., "Neural stem cells in the adult human brain" Exp. Cell. Res.: 253:733-6 (1999).
Mezey et al., "Turning blood into brain: cells bearing neuronal antigens generated in vivo from bone marrow" Science; 290:1779-82 (2000).
Morshead et al., "Hematopoietic competance is a rare property of neural stem cells that may depend on genetic and apigenetic alterations" Nat. Med.; 8:268-73 (2002).
Peterson et al., "Bone marrow as a potential source of hapetic oval cells" Science; 264:1168-70 (1999).
Scintu et al., "Differentiation of human bone marrow stem cells into cells with a natural phenotype: diverse effects of two specific treatments" BMC Neurosci.; 7:14 (2006).
U.S. Patent and Trademark Office, Office Action dated Jun. 24, 2005 in related U.S. Appl. No. 10/040,757.
U.S. Patent and Trademark Office, Office Action and 892 dated Jun. 27, 2006 in related U.S. Appl. No. 10/467,963.
U.S. Patent and Trademark Office, Office Action dated Oct. 15, 2009 in related U.S. Appl. No. 10/467,963.
U.S. Patent and Trademark Office, Office Action and 892 dated Apr. 7, 2008 in related U.S. Appl. No. 11/151,689.
U.S. Patent and Trademark Office, Office Action dated Jan. 4, 2008 in related U.S. Appl. No. 11/238,234.
U.S. Patent and Trademark Office, Office Action dated Aug. 29, 2006 in related U.S. Appl. No. 11/238,234.
U.S. Patent and Trademark Office, Office Action and 892 dated Apr. 3, 2007 in related U.S. Appl. No. 11/238,234.
U.S. Patent and Trademark Office, Office Action dated Oct. 7, 2008 in related U.S. Appl. No. 11/238,234.
Communication and 1449, filed Oct. 2, 2007 in related U.S. Appl. No. 11/238,234, and supplemental 1449 submitted on Oct. 4, 2007.
Information Disclosure Statement, Second Communication and PTO/SB/08b, filed Dec. 24, 2008 in related U.S. Appl. No. 11/238,234.
Yuan et al., Dev Neurosci 25:72-78 (2003).
International Search Report for PCT/IB2008/003868.
Flaim, C. et al., "Combinationial signaling microenvironments for studyinh stem cell fate" Stem Cells and Development (2008).
Tsuchida, K., Activins, Myostatin and Related TGF-β Family Members as Noval Therapeutic Targets for Endocrine, Metabolic and Immune Disorders (2004).
Endo, D., et al., "Activin or Follisatin: Which is More Beneficial to Support Liver Regeneration After Massive Hepatectomy?" (2006).
Albano, R., et al., Follistatin expression in ES and FS cells and in praimplantation mouse embryos: (1994).
U.S. Patent and Trademark Office, Office Action and Form 892 dated Jul. 17, 2014 in related U.S. Appl. No. 14/031,971.
U.S. Patent and Trademark Office, Office Action and Form 892 dated Nov. 22, 2013, in related U.S. Appl. No. 13/126,834.
Soto-Gutierrez, A., et al. Nature Biotech (2008) vol. 24(11); pp. 1412-1419.
Latella, L., et al. Cell Death and Differentiation (2000) vol. 7; pp. 145-154.
D'Amour, K.A., et al. Nature Biotechnology (2005) vol. 23(12); pp. 1534-1541.
Brevini, T.A.L., et al. Theriogenology (2010) vol. 74; pp. 544-550.
Paris, D.B.B.P., et al. Theriogenology (2010) vol. 74; pp. 516-524.
Munoz, M., et al. Theriogenology (2008) vol. 69; pp. 1159-1164.
Petitte, J.N., et al. Mech. of devlop. (2004) vol. 121; pp. 1159-1168.
Lavial, F., et al. Devlop. Growth & Diff. (2010) vol. 52; pp. 101-114.
Liu, S-Y., et al. Exp. Neurology (2004) vol. 190; pp. 109-121.
Kosaka, N., et al. FASEB Journal (2006) vol. 20; pp. E623-E629.
Kubo, A., et al. Dev. and Disease (2004) vol. 131; pp. 1651-1662.
Takahashi, K., et al. Cell (2007) vol. 131; pp. 861-872.
Smolich, B.D., et al. Molecular Biology of the Cell (1993) vol. 4; pp. 1267-1275.
Asashima, M., et al. Roux's Archives of Dev. Biology (1990) vol. 198; pp. 330-335.

(56) References Cited

OTHER PUBLICATIONS

Reijo Pera, R., et al. Differentiation (2009) vol. 78; pp. 18-23.
Reubinoff, B.E., et al. Nature Biotech. (2000) vol. 18; pp. 399-404.
Ireland, K.A. Visualizing Human Biology, 3rd Ed., Wiley and Sons, Inc. (2008); 3 pages.
Si-Tayeb, K., et al. Hepatology (2010) vol. 61, No. 1; pp. 297-305.
Cai, J., et al. Hepatology (2007) vol. 45, No. 5; pp. 1229-1239.
International Search Report for corresponding application PCT/IB2011/002200 (dated Jan. 13, 2012).
Decision on Motions; Patent Interference No. 105,953 SGL, Tech Center 1800; filed Sep. 26, 2014.
Sancho-Bru et al., Directed differentiation of murine-induced pluripotent stem cells to functional hepatocyte-like cells. Journal of Hepatology, vol. 54 (2011) pp. 98-107.
Nonaka et al., Development of murine hepatic sinusoidal endothelial cells characterized by the expression of hyaluronan receptors. Developmental Dynamics, vol. 236 (2007) pp. 2258-2267.
Asahina et al., Mesenchymal origin of hepatic stellate cells, submesothelial cells, and perivascular mesenchymal cells during mouse liver development. Hepatology, vol. 49, No. 3 (2009) pp. 998-1011.
U.S. Patent and Trademark Office, Office Action & PTO 892 dated Sep. 11, 2014 in related U.S. Appl. No. 13/162,228.

| | Functional characteristics | |
|---|---|---|
| Healthy liver | Fenestrated, Scavenger function, Factor VIII release; no tight junctions | $CD32b^+$, $Stab\text{-}1^+$, $Stab\text{-}2^+$, $L\text{-}SIGN^+$, $MRC1^+$ |
| Activated | Loss of fenestrations, production of a basement membrane, compromised scavenger function; tight junction formation | $CD32b^-$, $CD31^+$ (surface); increased VCAM-1 |

| | Functional characteristics | Markert expression |
|---|---|---|
| Quiescent | Retinol storage, non-fibrilar ECM synthesis | Vitamin A$^+$, PPARg$^+$, GFAP$^+$, GPR91$^+$, ALCAM, CRBP$^{high}$, p75NTR$^+$, COL1a1$^{high}$, TIMP-1$^{low}$ |
| Activated | Collagen 1a1 production, contraction, migration, cytokine release | Vitamin A$^-$, aSMA$^+$, Myh11$^+$, Lox$^+$, CRBP$^{low}$, GPR91$^-$, PPARg$^-$, COL1a1$^{high}$, TIMP-1$^{high}$ Fibronectin$^+$, |

FIG. 5A

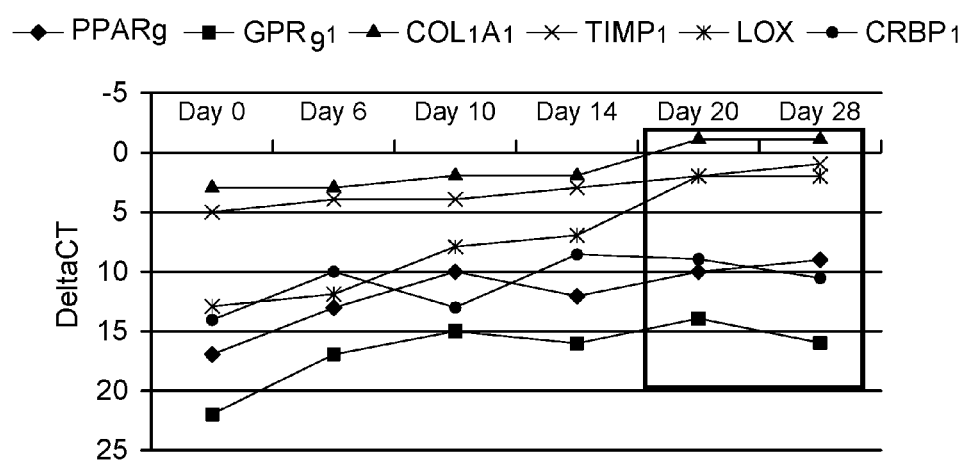

FIG. 5B

METHODS FOR DIFFERENTIATING CELLS INTO HEPATIC STELLATE CELLS AND HEPATIC SINUSOIDAL ENDOTHELIAL CELLS, CELLS PRODUCED BY THE METHOD, AND METHODS FOR USING THE CELLS

FIELD OF THE INVENTION

The invention is directed to methods for culturing cells so that the cells are induced to differentiate into cells that express a hepatic stellate phenotype and cells that express a hepatic sinusoidal endothelial phenotype. The invention is also directed to cells produced by the methods of the invention. The cells are useful, among other things, for treatment of liver deficiency, liver metabolism studies, and liver toxicity studies.

BACKGROUND OF THE INVENTION

Liver failure remains a devastating syndrome resulting from the loss of hepatic cell mass below a critical level. Although the prognosis of patients is greatly improved by orthotopic liver transplantation, treatment is limited by worldwide shortages of donor organs. In order to overcome these problems, alternative approaches, such as bio-artificial liver devices, albumin dialysis and cellular based therapy are being evaluated. In recent years, the feasibility to repopulate the liver with different cell types, such as mature and fetal hepatocytes, embryonic stem cells, intrahepatic progenitor cells and bone marrow derived cells, have been assessed in various animal models of liver disease.

Liver Development

Mouse embryonic and fetal liver development can be divided into different consecutive steps. During gastrulation (ED6-ED6.5), future definitive endodermal and mesodermal cells migrate through the primitive streak, located at the prospective posterior and proximal-lateral pole of the embryo. First, anterior endodermal cells ingress the primitive streak, migrate towards the distal tip of the epiblast cup and displace the visceral endoderm. The mesoderm migrates between the epiblast and endoderm. Definitive endoderm is characterized by the transient expression of primitive streak markers (LHX1, MIXL1, WNT3, LHX1, brachyury) and CXCR4, Sox17, HNF3b, Goosecoid and E-Cadherin. In contrast, primitive endoderm (visceral and parietal endoderm), which gives rise to the yolk sac, expresses Sox17, Sox7, and HNF3B. After gastrulation, embryonic progenitors of the digestive and respiratory organs initially exist in a single cell thick, epithelial sheet of endoderm that lines the ventral surface of the embryo. Then, the endoderm folds into a gut tube to form the foregut, midgut and hindgut endoderm. At ED8.25, ventral foregut is guided towards a hepatic fate under the influence of cytokines secreted by the adjacent cardiac mesoderm (aFGF-bFGF) and septum transversum mesenchyme (BMPs). After this specification (ED0.5-ED10), the resident cells of the primitive liver bud, consisting of bipotential hepatoblasts, undergo balanced events including proliferation, apoptosis, and differentiation to eventually constitute a functioning organ. This further maturation occurs through fibroblast growth factors (aFGF-FGF4-FGF8), Wnt signaling, factors secreted by the invading endothelial cells, the transiently (ED10) present hematopoietic cells in the fetal liver (Oncostatin M) and from the surrounding non-parenchymal cells (HGF). At ED14, bipotential hepatoblast become either fully mature hepatocytes or cholangiocytes. This determination depends upon the TGBβ/Activin and Notch2/Jagged1 signaling pathway.

Hepatic stellate cells (HSC): reside in perisinusoidal recesses between adjacent hepatocytes and represent ±8% of the liver. They project long processes (~50 μm) in the space of Disse and between adjacent hepatocytes. In the adult liver, HSC are quiescent, produce small amounts of ECM and store vitamin A in the form of retinyl esters in lipid droplets. HSC secrete many cytokines and virtually all growth factors. Not only do the cells secrete the cytokines, they also respond to them. Under pathological conditions, HSC are activated to become myofibroblast-like cells. They proliferate, acquire contractile properties, lose their capacity to store vitamin A and produce excessive amounts of ECM, causing scar formation. This activation is accompanied by changes in gene and miRNA expression, phenotype and function. If the liver injury is limited, HSC revert to a quiescent state or die by apoptosis. However, after prolonged injury, HSC become resistant to apoptosis and their activated phenotype may not be reversible.

HSC can be isolated from normal livers by taking advantage of their high content of lipid droplets that are rich in vitamin A. These lipid droplets are fluorescent under UV light allowing isolation of quiescent HSC by FACS. Moreover, due to their low density it is also possible to isolate them by gradient centrifugation. HSC isolated from normal livers have a quiescent phenotype showing a limited proliferative capacity in culture. Culture conditions for maintaining the quiescent phenotype for an extensive period of time are not known. After 24-48 hours in culture, the cells acquire most of the phenotypic and functional characteristics of activated HSC in injured liver, although their phenotype is not completely identical. When cultured under activating conditions human HSC can be expanded up to 20 doublings.

Liver fibrosis, which is the outcome of persistent hepatic inflammation, if left unmanaged, has serious long-term consequences for patient morbidity and mortality. Antifibrotic therapies must be aimed at inhibiting the activated hepatic stellate cell, which is responsible for the fibrotic response to injury. Development of specific anti liver-fibrosis drugs is, however, hampered by the fact that large numbers of quiescent human hepatic stellate cells, the chief cell responsible for liver fibrosis, are not available, as most isolated cell populations are culture-expanded, during which they quickly acquire an activated cell phenotype (Friedman et al., *J Biol Chem* 264:10756-10762 (1989); Friedman S. L., *Hepatology* 40:1041-1043 (2004)).

Hepatic sinusoidal endothelial cells (HSEC) comprise 20% of all liver cells and are strongly fenestrated cells. HSEC use these fenestrae (75-250 nm) to exclude larger particles and cells from the space of Disse but can also eliminate soluble macromolecules and colloidal particles from blood by active scavenging via specific endocytic receptors. The basement membrane underneath HSEC differs from other endothelia in that basement matrix molecules are present but not organized in a structure visible by transmission EM. HSEC, together with HSC, control the vascular tone in the sinusoidal capillaries. Under pathological conditions, e.g. in cirrhosis, HSEC undergo dramatic changes (collectively called 'capillarisation'): the fenestrated sieve-like endothelium is replaced by a classical closed capillary endothelium, with a dense basal lamina visible by EM. This results in reduced access of hepatocytes to $O_2$ and nutrients. Also, upon ageing, the HSEC undergo phenotypical changes, called 'pseudo-capillarisation', characterized by defenestration, basement membrane deposition and functional deterioration.

Aside from HSEC, liver also contains non-sinusoidal endothelium (in hepatic arteries and veins) and the lymphatic endothelium. Each of these can be distinguished by a separate combination of surface markers. The three major HSEC endocytosis receptors are among the group of unique and specific markers of these cells: i) Stab-2=the major scavenger receptor of HSEC[22]; ii) CD32b=SE-1=the unique FcγIIb receptor, the only Fc-receptor that mediates endocytosis, is present (in liver) only in HSEC; iii) the mannose receptor, clearing blood borne collagen alpha chains (=denatured collagen of several collagen types) and macromolecules and colloids that carry terminal mannose, ManNAc or GlcNAc residues. These receptors can be structurally identified by specific immune staining (live and fixed cells), or functionally by exposing intact cells to ligands for these three endocytosis receptors, which will accumulate the ligands only in HSEC. In addition, analogous to hepatocytes, within the sinusoidal endothelial population, differences have been detected in morphological and functional characteristics, depending on the location within the sinusoid ('zonation'): HSEC from the periportal region are less fenestrated, have a low cytoplasmic porosity index and efficiently bind wheat germ agglutinin (WGA), while those in the perivenous region are highly fenestrated, have a high cytoplasmic porosity index and only weakly bind WGA.

As is true for hepatocytes and HSC, culture of HSEC leads very quickly to de-differentiation and/or activation, whereby many functional attributes from the cells are lost. For instance, HSEC lose their endocytic ability after only a few hours of culture. This rapid loss of the "signature" scavenger function of HSEC in vitro may be significantly counteracted by specially designed culture media and physiological $O_2$ tension. In addition, co-culturing of hepatocytes, HSEC and HSC has proven fruitful in maintenance of their "in vivo" phenotype.

SUMMARY OF THE INVENTION

The invention is based on methods developed by the inventors to produce a renewable source of hepatic stellate cells and hepatic sinusoidal endothelial cells in vitro.

Related application PCT/IB08/003868 discloses a four-step differentiation protocol for producing cells having a hepatocyte phenotype. Step (a) can begin with cells expressing a primitive endodermal phenotype and are induced to express a definitive endodermal phenotype. In Step (b), cells that express a definitive endodermal phenotype can then be induced into cells that express a liver-committed endodermal phenotype. In Step (c), cells that express a liver-committed phenotype are induced to express a hepatoblast phenotype. In Step (d), cells that express a hepatoblast phenotype are induced into cells that express a hepatic phenotype.

Subsequently, the inventors unexpectedly found that this method also produces cells with a hepatic stellate cell phenotype and cells that express a hepatic sinusoidal endothelial cell phenotype. Numbered statements of the invention are as follows.

1. A method for inducing cells to differentiate into cells with a hepatic stellate phenotype and cells with a hepatic sinusoidal endothelial phenotype, comprising:
   (a) culturing cells with about 5 ng/ml to about 500 ng/ml Wnt3a and about 10 ng/ml to about 1,000 ng/ml ActivinA;
   (b) then culturing the cells of step (a) with about 1 ng/ml to about 100 ng/ml bFGF and about 5 ng/ml to about 500 ng/ml BMP4;
   (c) then culturing the cells of step (b) with about 5 ng/ml to about 500 ng/ml aFGF, about 1 ng/ml to about 100 ng/ml FGF4 and about 2.5 ng/ml to about 250 ng/ml FGF8b; and
   (d) then culturing the cells of step (c) with about 2 ng/ml to about 200 ng/ml HGF and about 10 ng/ml to about 1,000 ng/ml Follistatin.

2. The method of statement 1, wherein the cells are cultured in step (a) with about 50 ng/ml Wnt3a and about 100 ng/ml ActivinA.

3. The method of statement 1, wherein the cells are cultured in step (b) with about 10 ng/ml bFGF and about 50 ng/ml BMP4.

4. The method of statement 1, wherein the cells are cultured in step (c) with about 50 ng/ml aFGF, about 10 ng/ml FGF4 and about 25 ng/ml FGF8b.

5. The method of statement 1, wherein the cells are cultured in step (d) with about 20 ng/ml HGF and about 100 ng/ml Follistatin.

6. A method for inducing cells to differentiate into cells with a hepatic stellate phenotype and cells with a hepatic sinusoidal endothelial phenotype, comprising:
   (a) culturing the cells with about 50 ng/ml Wnt3a and about 100 ng/ml ActivinA;
   (b) then culturing the cells of step (a) with about 10 ng/ml bFGF and about 50 ng/ml BMP4;
   (c) then culturing the cells of step (b) with about 50 ng/ml aFGF, about 10 ng/ml FGF4 and about 25 ng/ml FGF8b; and
   (d) then culturing the cells of step (c) with about 20 ng/ml HGF and about 100 ng/ml Follistatin.

7. Cells produced according to any of the methods described herein.

8. The methods herein, wherein the cells are cultured at one or more steps in a medium containing about $10^{-4}$ M to about $10^{-7}$ M dexamethasone.

9. The method of statement 8, wherein the cells are cultured at one or more steps in a medium containing about $10^{-6}$ M dexamethasone.

10. The methods herein, wherein the cells are cultured at one or more steps in a medium containing about $10^{-5}$ M to about $10^{-10}$ M dexamethasone.

11. The methods herein, wherein the cells are cultured at one or more steps for at least four days.

12. The methods herein, wherein step (a) is about six days, step (b) is about four days, step (c) is about four days, and step (d) is about seven to fourteen days.

13. The methods herein, wherein the cells are mammalian.

14. The method of statement 13, wherein the cells are human, mouse, or rat.

15. The methods herein, wherein the cells that are contacted with Wnt3A and Activin A are embryonic stem cells or cells that are not embryonic stem cells, embryonic germ cells or germ cells, and can differentiate into at least one cell type of each of the endodermal, ectodermal and mesodermal embryonic lineages.

16. The method of statement 15, wherein the cells are not embryonic germ cells, embryonic stem cells or germ cells, and can differentiate into at least one cell type of each of the endodermal, ectodermal and mesodermal embryonic lineages.

17. The method of statement 16, wherein the cells are IPS cells.

18. The method of statement 15, wherein the cells are embryonic stem cells.

19. The method of statement 16, wherein the cells used in step (a) are isolated from bone marrow, placenta, umbilical cord, muscle, brain, liver spinal cord, blood or skin. But they can be derived from any tissue or cell, and also by de-differentiation.

20. The methods herein, wherein the cells are cultured at one or more steps in a medium containing a serum concentration ranging from about 0% to about 2%; in one embodiment, from about 0.5% to about 2%.

21. The method of statement 20, wherein the cells are cultured at one or more steps in a medium containing a serum concentration of about 2%. In one embodiment, step (a) is about 2% and the remaining steps are about 0.5%.

22. The methods above further comprising isolating hepatic stellate cells and/or hepatic endothelial sinusoidal cells produced by the differentiation protocol.

23. A pharmaceutical composition comprising the cells produced according to any one of the methods herein.

24. A method of treatment comprising administering a therapeutically effective amount of the cells produced according to any one of the methods herein to a subject with a liver deficiency.

Cells with a hepatic stellate phenotype and cells with a hepatic endothelial sinusoidal phenotype begin to be produced in the first step of the method when the cells used in step (a) are incubated with a combination of activinA and Wnt3a. Accordingly, those cells can be isolated after this or after any of the following steps. However, as exemplified by human embryonic stem cells in the Examples below, the genes indicating these two phenotypes reaches a peak at about day 21. Accordingly, these cells may also be isolated at later stages in the differentiation protocol, such as on days 21-28 or longer.

The methods described herein can be carried out with or without serum. This may depend on the species of the pluripotent cell that is being differentiated, such as rodent, human, etc. In one embodiment, the serum is fetal bovine serum. Whether serum is required can be determined empirically.

In one embodiment, culturing cells with Wnt3a is about 2.5 days with a range of about 1.5-3.5 days, such as 2 or 3 days.

In a further embodiment of the invention, the cells may be subjected to a modification of the method described above. In particular, the differentiation protocol may not require bFGF, aFGF, FGF4, or FGF8b. Accordingly, in step (a), which can be from about day 0 to about day 5, cells can be incubated with activinA and Wnt3a. In step (b), the cells are exposed to BMP4, which can be from about day 6. In step (c), the cells are exposed to HGF and Follistatin which can be from about day 14 until about day 21-28. This method is exemplified with human ESCs.

Any cell can be used in the initial step of culture with Wnt3a and Activin A as long as it has a phenotype of a cell that is prior to the primitive streak. Such a cell could express Oct3/4. For an embryonic stem cell, for example, the phenotype would be inner cell mass cell or epiblast. Cells include, but are not limited to, primordial germ cells, embryonic germ cells, cells produced by somatic cell nuclear transplantation into oocytes, tumor cell lines, embryonal carcinoma cells, blastomere cells, inner cell mass cells, embryonic stem cell cultures and lines, spermatogonial stem cells, epiblast cells, and other non-embryonic stem cells, such as reprogrammed somatic cells (IPSC). In one embodiment, such cells express Oct3/4 at levels greater than about 0.1% of Oct3/4 expression in embryonic stem cells.

Cells include, but are not limited to, cells that are not embryonic stem cells and not germ cells, having some characteristics of embryonic stem cells, but being derived from non-embryonic tissue. Such cells have been referred to as "MAPC." This acronym describes a class of non-embryonic somatic cells as further detailed below.

The cells ("MAPC") may express pluripotency markers, such as oct4. They may also express markers associated with extended replicative capacity, such as telomerase. Other characteristics of pluripotency can include the ability to differentiate into cell types of more than one germ layer, such as two or three of ectodermal, endodermal, and mesodermal embryonic germ layers. Such cells may or may not be immortalized or transformed in culture. The cells may be highly expanded without being transformed and also maintain a normal karyotype. For example, in one embodiment, the non-embryonic stem, non-germ cells may have undergone at least 10-40 cell doublings in culture, such as 50, 60, or more, wherein the cells are not transformed and have a normal karyotype. The cells may differentiate into at least one cell type of each of two of the endodermal, ectodermal, and mesodermal embryonic lineages and may include differentiation into all three. Further, the cells may not be tumorigenic, such as not producing teratomas. If cells are transformed or tumorigenic, and it is desirable to use them for infusion, such cells may be disabled so they cannot form tumors in vivo, as by treatment that prevents cell proliferation into tumors. Such treatments are well known in the art.

Cells ("MAPC") include, but are not limited to, the following numbered embodiments:

1. Isolated expanded non-embryonic stem, non-germ cells, the cells having undergone at least 10-40 cell doublings in culture, wherein the cells express oct4, are not transformed, and have a normal karyotype.

2. The non-embryonic stem, non-germ cells of 1 above that further express one or more of telomerase, rex-1, rox-1, or sox-2.

3. The non-embryonic stem, non-germ cells of 1 above that can differentiate into at least one cell type of at least two of the endodermal, ectodermal, and mesodermal embryonic lineages.

4. The non-embryonic stem, non-germ cells of 3 above that further express one or more of telomerase, rex-1, rox-1, or sox-2.

5. The non-embryonic stem, non-germ cells of 3 above that can differentiate into at least one cell type of each of the endodermal, ectodermal, and mesodermal embryonic lineages.

6. The non-embryonic stem, non-germ cells of 5 above that further express one or more of telomerase, rex-1, rox-1, or sox-2.

7. Isolated expanded non-embryonic stem, non-germ cells that are obtained by culture of non-embryonic, non-germ tissue, the cells having undergone at least 40 cell doublings in culture, wherein the cells are not transformed and have a normal karyotype.

8. The non-embryonic stem, non-germ cells of 7 above that express one or more of oct4, telomerase, rex-1, rox-1, or sox-2.

9. The non-embryonic stem, non-germ cells of 7 above that can differentiate into at least one cell type of at least two of the endodermal, ectodermal, and mesodermal embryonic lineages.

10. The non-embryonic stem, non-germ cells of 9 above that express one or more of oct4, telomerase, rex-1, rox-1, or sox-2.

11. The non-embryonic stem, non-germ cells of 9 above that can differentiate into at least one cell type of each of the endodermal, ectodermal, and mesodermal embryonic lineages.

12. The non-embryonic stem, non-germ cells of 11 above that express one or more of oct4, telomerase, rex-1, rox-1, or sox-2.

13. Isolated expanded non-embryonic stem, non-germ cells, the cells having undergone at least 10-40 cell doublings in culture, wherein the cells express telomerase, are not transformed, and have a normal karyotype.

14. The non-embryonic stem, non-germ cells of 13 above that further express one or more of oct4, rex-1, rox-1, or sox-2.

15. The non-embryonic stem, non-germ cells of 13 above that can differentiate into at least one cell type of at least two of the endodermal, ectodermal, and mesodermal embryonic lineages.

16. The non-embryonic stem, non-germ cells of 15 above that further express one or more of oct4, rex-1, rox-1, or sox-2.

17. The non-embryonic stem, non-germ cells of 15 above that can differentiate into at least one cell type of each of the endodermal, ectodermal, and mesodermal embryonic lineages.

18. The non-embryonic stem, non-germ cells of 17 above that further express one or more of oct4, rex-1, rox-1, or sox-2.

19. Isolated expanded non-embryonic stem, non-germ cells that can differentiate into at least one cell type of at least two of the endodermal, ectodermal, and mesodermal embryonic lineages, said cells having undergone at least 10-40 cell doublings in culture.

20. The non-embryonic stem, non-germ cells of 19 above that express one or more of oct4, telomerase, rex-1, rox-1, or sox-2.

21. The non-embryonic stem, non-germ cells of 19 above that can differentiate into at least one cell type of each of the endodermal, ectodermal, and mesodermal embryonic lineages.

22. The non-embryonic stem, non-germ cells of 21 above that express one or more of oct4, telomerase, rex-1, rox-1, or sox-2.

The invention is also directed to methods of using the cells produced by the methods for treatment of liver deficiencies.

The invention is also directed to methods of using the cells for studies of liver metabolism, for example, to identify or assess metabolic modulators.

The invention is also directed to methods of using the cells for studies of liver toxicity, for example, to identify or assess the toxicity of specific compounds.

The invention is also directed to pharmaceutical compositions containing the cells of the invention. Such compositions are suitable for administration to subjects in need of such cells. The cells would be administered in therapeutically effective amounts.

The hepatic stellate cells and the hepatic sinusoidal endothelial cells may play a role during hepatocyte differentiation and support hepatocyte function in vivo and in vitro. Therefore, these cells may be used adjunctively to hepatocytes in in vivo and in vitro methods, such as treatment of liver deficiencies, assays for liver toxicity, identification of metabolic modulators, etc., as disclosed in this application.

The HSCs and LSECs can be used in drug discovery methods to screen for agents that are metabolic modulators or otherwise affect the function or phenotype of the cells, such as agents that are toxic to the cells. Such agents include, but are not limited to, small organic molecules, antisense nucleic acids, siRNA, DNA aptamers, peptides, antibodies, non-antibody proteins, cytokines, chemokines, and chemoattractants. The cells are exposed to the agent and the effect is compared or measured against the normal function/phenotype.

BRIEF DESCRIPTION OF THE FIGURES

FIGS. 5A and 5B. Expression of hepatic stellate genes (quiescent and some non-quiescent) is found maximally at d20. Human ESC were cultured sequentially with Activin A/Wnt3a, BMP4/FGF2, FGF1, 4 and 8, and HGF/Follistatin, in 2% serum on matrigel coated plates for 28 days. On d0, 6, 10, 14, 20 and 28, cells were harvested and transcripts found in quiescent and activated hepatic stellate cells (HSC) (see table, (A)) quantified using RT-qPCR. The results show that there is maximal up-regulation of stellate cell genes on day 20 of differentiation (shown in graph, (B)).

DETAILED DESCRIPTION OF THE INVENTION

Definitions

Figure 1A:
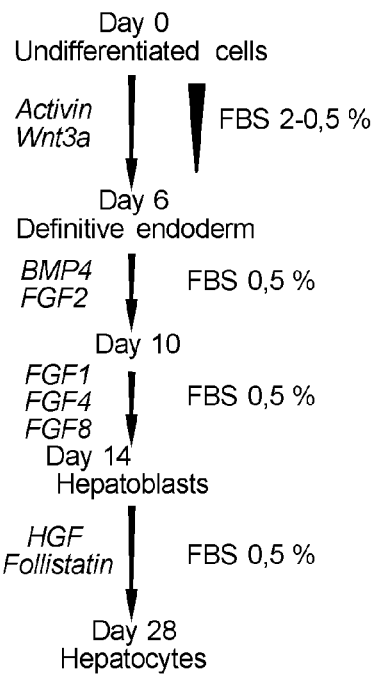
FIGS. 1A-1C. Gene expression analysis (hepatocytes) at early stages of differentiation. (A) Schematic diagram of the differentiation protocol for mouse IPSC. (B) Gene expression analysis by real-time RT-PCR of key genes expressed in primitive streak/mesendoderm at day 0, 2, 4, 6 and 10 of differentiation and (C) gene expression analysis by real-time RT-PCR of key genes expressed in definitive endoderm and primitive endoderm at day 0, 2, 4, 6 and 10 of differentiation. Results are shown as mean fold change respect to day 0±standard deviation of three independent differentiations.

"A" or "an" means one or more than one.

"Co-administer" means to administer in conjunction with one another, together, coordinately, including simultaneous or sequential administration of two or more agents.

"Comprising" means, without other limitation, including the referent, necessarily, without any qualification or exclusion on what else may be included. For example, "a composition comprising x and y" encompasses any composition that contains x and y, no matter what other components may be present in the composition. Likewise, "a method comprising the step of x" encompasses any method in which x is carried out, whether x is the only step in the method or it is only one of the steps, no matter how many other steps there may be and no matter how simple or complex x is in comparison to them. "Comprised of" and similar phrases using words of the root "comprise" are used herein as synonyms of "comprising" and have the same meaning.

"Definitive endodermal phenotype" is a particular phenotype of cells that no longer express the self-renewal gene Oct3/4, do not express the primitive endoderm gene Sox7, do not express the mesodermal gene Flk1, but express Sox17, Foxa2, E-cadherin, CXCR4, and PDGF-Ra.

"Effective amount" generally means an amount which provides the desired local or systemic effect. For example, an effective amount is an amount sufficient to effectuate a beneficial or desired clinical result. The effective amounts can be provided all at once in a single administration or in fractional amounts that provide the effective amount in several administrations. The precise determination of what would be considered an effective amount may be based on factors individual to each subject, including their size, age, injury, and/or disease or injury being treated, and amount of time since the injury occurred or the disease began. One skilled in the art will be able to determine the effective amount for a given subject based on these considerations which are routine in the art. As used herein, "effective dose" means the same as "effective amount."

"Effective route" generally means a route which provides for delivery of an agent to a desired compartment, system, or location. For example, an effective route is one through which an agent can be administered to provide at the desired site of action an amount of the agent sufficient to effectuate a beneficial or desired clinical result.

"EC cells" were discovered from analysis of a type of cancer called a teratocarcinoma. In 1964, researchers noted that a single cell in teratocarcinomas could be isolated and remain undifferentiated in culture. This type of stem cell became known as an embryonic carcinoma cell (EC cell).

"Embryonic Stem Cells (ESC)" are well known in the art and have been prepared from many different mammalian species for many years. Embryonic stem cells are stem cells derived from the inner cell mass of an early stage embryo known as a blastocyst. They are able to differentiate into all derivatives of the three primary germ layers: ectoderm, endoderm, and mesoderm. These include each of the more than 220 cell types in the adult body. The ES cells can become any tissue in the body, excluding placenta. Only the morula's cells are totipotent, able to become all tissues and a placenta.

"Hepatic differentiation factors" are chemical or biological factors that induce differentiation of stem and progenitor cells into more differentiated cells of the hepatic lineage. Hepatic differentiation factors include, but are not limited to, Wnt3a, ActivinA, bFGF, BMP4, aFGF, FGF4, FGF8b, HGF and Follistatin. The initial cell may express Oct3/4.

"Hepatoblast phenotype" is a particular phenotype of cells that co-express albumin, alpha fetoprotein and keratin 19, and express, on the cell membrane, c-Met, EPCAM, and DM (Tanimizu, N. et al., *J Cell Sci*, 116:1775-1786 (2003)).

"Hepatocyte phenotype" is a particular phenotype of cells that express albumin and keratin 18 but not alpha fetoprotein and keratin 19; in addition, hepatocytes may express one or more of TAT, MRP2, G6P, GLYS2, PEPCK, A1AT, BSEP, CX-32, NTCP, CYP7A1 (rat) and CYP3A4 (human).

"Hepatic stellate cells" may be isolated and identified by genes including, but not limited to, one or more of those listed in FIG. 5, expressed by these cells.

Figures 4A, 4B:
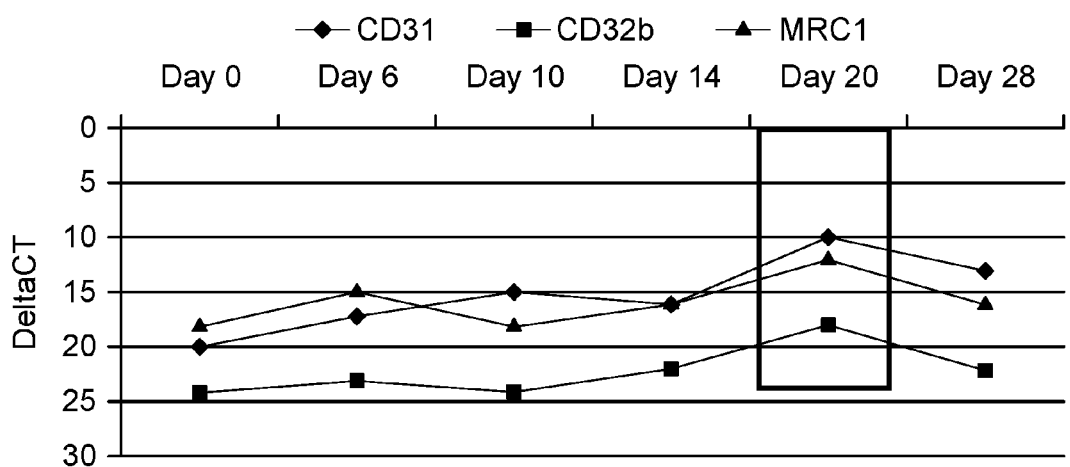
FIGS. 4A and 4B. Expression of (hepatic sinusoidal) endothelial genes is found maximally at d20. Human ESC were cultured sequentially with Activin A/Wnt3a, BMP4/FGF2, FGF1, 4 and 8, and HGF/Follistatin, in 2% serum on matrigel coated plates for 28 days. On d0, 6, 10, 14, 20 and 28, cells were harvested and transcripts found in healthy liver derived of activated hepatic sinusoidal endothelial cells (HSEC) (see table, (A)) quantified using RT-qPCR. The results show that there is maximal up-regulation of HSEC genes on day 20 of differentiation (shown in graph, (B)).

"Hepatic sinusoidal endothelial cells" can be identified by genes including, but not limited to, one of those listed in FIG. 4, expressed by these cells.

Use of the term "includes" is not intended to be limiting. For example, stating that an inhibitor "includes fragments and variants does not mean that other forms of the inhibitor are excluded.

"Induced pluripotent stem cells (IPSC or IPS cells)" is a designation that pertains to somatic cells that have been reprogrammed, for example, by introducing exogenous genes that confer on the somatic cell a less differentiated phenotype. These cells can then be induced to differentiate into less differentiated progeny. IPS cells have been derived using modifications of an approach originally discovered in 2006 (Yamanaka, S. et al., *Cell Stem Cell*, 1:39-49 (2007)). For example, in one instance, to create IPS cells, scientists started with skin cells that were then modified by a standard laboratory technique using retroviruses to insert genes into the cellular DNA. In one instance, the inserted genes were Oct4, Sox2, Lif4, and c-myc, known to act together as natural regulators to keep cells in an embryonic stem cell-like state. These cells have been described in the literature. See, for example, Wernig et al., *PNAS*, 105:5856-5861 (2008); Jaenisch et al., *Cell*, 132:567-582 (2008); Hanna et al., *Cell*, 133:250-264 (2008); and Brambrink et al., *Cell Stem Cell*, 2:151-159 (2008). It is also possible that such cells can be created by specific culture conditions (exposure to specific agents), as is described in the Examples in this application. These references are all incorporated by reference for teaching IPSCs and methods for producing them.

IPS cells have many characteristic features of embryonic stem cells. For example, they have the ability to create chimeras with germ line transmission and tetraploid complementation and they can also form teratomas containing various cell types from the three embryonic germ layers. On the other hand, they may not be identical as some reports demonstrate. See, for example, Chin et al., *Cell Stem Cell* 5:111-123 (2009) showing that induced pluripotent stem cells and embryonic stem cells can be distinguished by gene expression signatures.

The term "isolated" refers to a cell or cells that are not associated with one or more cells or one or more cellular components that are associated with the cell or cells in vivo. An "enriched population" means a relative increase in numbers of a desired cell relative to one or more other cell types in vivo or in primary culture.

However, as used herein, the term "isolated" does not indicate the presence of only a specific desired cell, such as a stem or hepatic progenitor cell. Rather, the term "isolated" indicates that the cells are removed from their natural tissue environment and are present at a higher concentration as compared to the normal tissue environment. Accordingly, an "isolated" cell population may further include cell types in addition to stem cells and may include additional tissue components. This also can be expressed in terms of cell doublings, for examples. A cell may have undergone 10, 20, 30, 40 or more doublings in vitro or ex vivo so that it is enriched compared to its original numbers in vivo or in its original tissue environment (e.g., bone marrow, peripheral blood, adipose tissue, etc.)

"Liver-committed endodermal phenotype" is a particular phenotype of cells that are EPCAM positive and Dlk1 Negative (Tanimizu, N. et al., *J Cell Sci*, 116:1775-1786 (2003)).

"MAPC" is an acronym for "multipotent adult progenitor cell." It refers to a cell that is not an embryonic stem cell or germ cell but has some characteristics of these. MAPC can be characterized in a number of alternative descriptions, each of which conferred novelty to the cells when they were discovered. They can, therefore, be characterized by one or more of those descriptions. First, they have extended replicative capacity in culture without being transformed (tumorigenic) and with a normal karyotype. Second, they may give rise to cell progeny of more than one germ layer, such as two or all three germ layers (i.e., endoderm, mesoderm and ectoderm) upon differentiation. Third, although they are not embryonic stem cells or germ cells, they may express markers of these primitive cell types so that MAPCs may express one or more of Oct 3/4 (i.e., Oct 3A), rex-1, and rox-1. They may also express one or more of sox-2 and SSEA-4. Fourth, like a stem cell, they may self-renew, that is, have an extended replication capacity without being transformed. This means that these cells express telomerase (i.e., have telomerase activity). Accordingly, the cell type that was designated "MAPC" may be characterized by alternative basic characteristics that describe the cell via some of its novel properties.

The term "adult" in MAPC is non-restrictive. It refers to a non-embryonic somatic cell. MAPCs are karyotypically normal and do not form teratomas in vivo. This acronym was first used in U.S. Pat. No. 7,015,037 to describe a pluripotent cell isolated from bone marrow. However, cells with pluripotential markers and/or differentiation potential have been discovered subsequently and, for purposes of this invention, may be equivalent to those cells first designated "MAPC." Essential descriptions of the MAPC type of cell are provided in the Summary of the Invention above.

MAPC represents a more primitive progenitor cell population than MSC (Verfaillie, C. M., *Trends Cell Biol* 12:502-8 (2002), Jahagirdar, B. N., et al., *Exp Hematol*, 29:543-56 (2001); Reyes, M. and C. M. Verfaillie, *Ann N Y Acad Sci*, 938:231-233 (2001); Jiang, Y. et al., *Exp Hematol*, 30896-904 (2002); and (Jiang, Y. et al., *Nature*, 418:41-9. (2002)).

The term "MultiStem®" is the trade name for a cell preparation based on the MAPCs of U.S. Pat. No. 7,015,037, i.e., a non-embryonic stem, non-germ cell as described above. MultiStem® is prepared according to cell culture methods disclosed in this patent application, particularly, lower oxygen and higher serum. MultiStem® is highly expandable, karyotypically normal, and does not form teratomas in vivo. It may differentiate into cell lineages of more than one germ layer and may express one or more of telomerase, oct3/4, rex-1, rox-1, sox-2, and SSEA4.

"Multipotent," with respect to the term in "MAPC," refers to the ability to give rise to cell lineages of more than one primitive germ layer (i.e., endoderm, mesoderm and ectoderm) upon differentiation, such as all three. This term is not used consistently in the literature.

"Pharmaceutically-acceptable carrier" is any pharmaceutically-acceptable medium for the cells used in the present invention. Such a medium may retain isotonicity, cell metabolism, pH, and the like. It is compatible with administration to a subject in vivo, and can be used, therefore, for cell delivery and treatment.

"Pluripotent" as used herein, with respect to hepatocyte differentiation, means any cell that, when exposed to Wnt3a and Activin A at the specified amounts, gives rise to cells with a definitive endodermal phenotype. Such cells may have the ability to give rise to cell lineages of more than one primitive germ layer (i.e., endoderm, mesoderm and ectoderm) upon differentiation, such as all three, as disclosed in this application. Accordingly, the term "pluripotent" is a convenience and really refers to any cell that has a phenotype of a cell that is prior to the primitive streak. In this application, the cell of step (a) may also be referred to a "undifferentiated." Again, this is a term of convenience to refer to a cell that is sufficiently undifferentiated as to be able to differentiate into hepatic stellate cells and hepatic sinusoidal endothelial cells when subjected to the differentiation methods described in this application.

"Primitive endodermal phenotype" is a particular phenotype of cells that may express sox7, sox17, gata4, gata6, Cited1, Tcf2, LamA1, Dab2, LamA1, LamA4, Lamc1, Co14a1, and Nidogen2 (this is a phenotype of mouse and rat MAPC, XEN cells from J. Rossant and Sox7 expressing ESC from J. Rossant. See also Ulloa-Montoya et al., *Genome Biol*, 8:R163 (2007); Se'guin et al., *Cell Stem Cell*, 3:182-195 (2008); and Kunath et al., *Development*, 132: 1649-1661 (2005)).

"Primordial embryonic germ cells" (PG or EG cells) can be cultured and stimulated to produce many less differentiated cell types.

"Progenitor cells" are cells produced during differentiation of a stem cell that have some, but not all, of the characteristics of their terminally-differentiated progeny. The term "progenitor" as used in the acronym "MAPC" does not limit these cells to a particular lineage. A hepatocyte progenitor is any cell in the hepatocyte lineage that is less differentiated than a hepatocyte.

The term "reduce" as used herein means to prevent as well as decrease. In the context of treatment, to "reduce" is to either prevent or ameliorate one or more clinical symptoms. A clinical symptom is one (or more) that has or will have, if left untreated, a negative impact on the quality of life (health) of the subject.

"Self-renewal" refers to the ability to produce replicate daughter stem cells having differentiation potential that is identical to those from which they arose. A similar term used in this context is "proliferation."

"Stem cell" means a cell that can undergo self-renewal (i.e., progeny with the same differentiation potential) and also produce progeny cells that are more restricted in differentiation potential. Within the context of the invention, a stem cell would also encompass a more differentiated cell that has dedifferentiated, for example, by nuclear transfer, by fusions with a more primitive stem cell, by introduction of specific transcription factors, or by culture under specific conditions. See, for example, Wilmut et al., *Nature*, 385: 810-813 (1997); Ying et al., *Nature*, 416:545-548 (2002); Guan et al., *Nature*, 440:1199-1203 (2006); Takahashi et al., *Cell*, 126:663-676 (2006); Okita et al., *Nature*, 448:313-317 (2007); and Takahashi et al., *Cell*, 131:861-872 (2007).

Dedifferentiation may also be caused by the administration of certain compounds or exposure to a physical environment in vitro or in vivo that would cause the dedifferentiation. Stem cells also may be derived from abnormal tissue, such as a teratocarcinoma and some other sources such as embryoid bodies (although these can be considered embryonic stem cells in that they are derived from embryonic tissue, although not directly from the inner cell mass).

"Subject" means a vertebrate, such as a mammal, such as a human. Mammals include, but are not limited to, humans, dogs, cats, horses, cows and pigs.

The term "therapeutically effective amount" refers to the amount determined to produce any therapeutic response in a mammal. For example, effective amounts of the therapeutic cells or cell-associated agents may prolong the survivability of the patient, and/or inhibit overt clinical symptoms. Treatments that are therapeutically effective within the meaning of the term as used herein, include treatments that improve a subject's quality of life even if they do not improve the disease outcome per se. Such therapeutically effective amounts are ascertained by one of ordinary skill in the art through routine application to subject populations such as in clinical and pre-clinical trials. Thus, to "treat" means to deliver such an amount.

"Treat," "treating" or "treatment" are used broadly in relation to the invention and each such term encompasses, among others, preventing, ameliorating, inhibiting, or curing a deficiency, dysfunction, disease, or other deleterious process, including those that interfere with and/or result from a therapy.

Methods and Compositions of the Invention

The methods of the invention induce cells in culture to progress through the appropriate stages of hepatic development, thus recapitulating hepatic development in vitro and, as a result, give rise to cells having hepatic stellate properties and cells having hepatic sinusoidal endothelial properties (e.g., biochemical and anatomical characteristics of these two hepatic cell types).

In one embodiment, culture methods comprise a sequential addition of hepatic differentiation factors to cells, wherein there is a first addition of about 5 ng/ml to about 500 ng/ml Wnt3a, more particularly about 50 ng/ml Wnt3a, and about 10 ng/ml to about 1,000 ng/ml ActivinA, more particularly about 100 ng/ml ActivinA; a second addition of about 1 ng/ml to about 100 ng/ml bFGF, more particularly about 10 ng/ml bFGF, and 5 ng/ml to about 500 ng/ml BMP4, more particularly about 50 ng/ml BMP4; a third addition of 5 ng/ml to about 500 ng/ml aFGF, more particularly about 50 ng/ml aFGF, about 1 ng/ml to about 100 ng/ml FGF4, more particularly about 10 ng/ml FGF4, and about 2.5 ng/ml to about 250 ng/ml FGF8b, more particularly about 25 ng/ml FGF8b; and a fourth addition of about 2 ng/ml to about 200 ng/ml HGF, more particularly about 20 ng/ml HGF, and about 10 ng/ml to about 1,000 ng/ml Follistatin, more particularly about 100 ng/ml Follistatin.

At each successive step, the culture is continued for at least four days. More particularly, the cells are cultured in the first step for about six days; in the second step for about four days; in the third step for about four days; and in the fourth step for about seven days. In one embodiment, cells are cultured with Wnt3a for about 2.5 days.

At one or more steps, the cells are cultured in a medium containing a serum concentration from 0% to about 2%, more particularly about 2%.

Additionally, at one or more steps, the cells are cultured in a medium containing about $10^{-4}$ M to about $10^{-7}$ M dexamethasone, more particularly about $10^{-6}$ M dexamethasone.

Culture medium at each successive step of the methods may contain only the growth factor(s) described for that step. Cells can be washed between each step to reduce the presence of previously added growth factor(s). Alternatively, reduced concentrations of the previously provided factor(s) in a previous step can remain in the culture medium of the next step. Or the factor(s) of the preceding step(s) could be inactivated.

The methods encompass the use of any Wnt3a, ActivinA, bFGF, BMP4, aFGF, FGF4, FGF8b, HGF and Follistatin known in the art and having conserved function, and from all species (e.g., orthologs from human, mouse, rat, monkey, pig and the like). The hepatic differentiation factors of the present invention are well known to those skilled in the art.

Suitable forms of Wnt3a, ActivinA, bFGF, BMP4, aFGF, FGF4, FGF8b, HGF and Follistatin include, but are not limited to, isolated polypeptides, which are optionally recombinant, including whole proteins, partial proteins (e.g., domains) and peptide fragments. Fragments of a polypeptide preferably are those fragments that retain the distinct functional capability of the particular factor, which in the present invention generally relates to the ability to influence hepatic differentiation (the specific function of each factor is well known in the art). Such polypeptides also include, but are not limited to, fusion proteins and chimeric proteins. Short polypeptides can be synthesized chemically using well-established methods of peptide synthesis.

Cytokines may be replaced by small molecules that activate the same signal pathway, such as GSK3b inhibitor for Wnt3a; kinase activating molecules for the FGFs.

The methods encompass a sequential addition of hepatic differentiation factors to cells.

In the first step, the hepatic differentiation factors Wnt3a and Activin A are added to the cells.

The concentration of Wnt3a that is added to the cells can range from about 5 ng/ml to about 500 ng/ml. However, the invention also encompasses sub-ranges of concentrations of Wnt3a. For example, from about 5-25 ng/ml, 25-50 ng/ml, 50-75 ng/ml, 75-100 ng/ml, 100-150 ng/ml, 150-300 ng/ml and 300-500 ng/ml. The preferred concentration of Wnt3a that is added to the cells is about 50 ng/ml. The duration of Wnt3a exposure used in the examples is six days. However, this may be changed to two, three, four, or five days.

The concentration of Activin A that is added to the cells can range from about 10 ng/ml to about 1000 ng/ml. However, the invention also encompasses sub-ranges of concentrations of Activin A. For example, from about 10-25 ng/ml, 25-50 ng/ml, 50-75 ng/ml, 75-100 ng/ml, 100-125 ng/ml, 125-150 ng/ml, 150-175 ng/ml, 175-200 ng/ml, 200-400 ng/ml, 400-600 ng/ml, 600-800 ng/ml and 800-1000 ng/ml. The preferred concentration of Activin A that is added to the cells is about 100 ng/ml. The duration of Activin A exposure used in the examples is six days. However, this may be changed to four, five, or seven days.

In the second step, the hepatic differentiation factors bFGF and BMP4 are added to the cells.

The concentration of bFGF that is added to the cells can range from about 1 ng/ml to about 100 ng/ml. However, the invention also encompasses sub-ranges of concentrations of bFGF. For example, from about 1-2 ng/ml, 2-4 ng/ml, 4-6 ng/ml, 6-8 ng/ml, 8-10 ng/ml, 10-12 ng/ml, 12-14 ng/ml, 14-16 ng/ml, 16-18 ng/ml, 18-20 ng/ml, 20-40 ng/ml, 40-60 ng/ml, 60-80 ng/ml and 80-100 ng/ml. The preferred concentration of bFGF that is added to the cells is about 10 ng/ml. The duration of bFGF exposure used in the examples is five days. However, this may be changed to four, six, or seven days.

The concentration of BMP4 that is added to the cells can range from about 5 ng/ml to about 500 ng/ml. However, the invention also encompasses sub-ranges of concentrations of BMP4. For example, from about 5-10 ng/ml, 10-20 ng/ml, 20-30 ng/ml, 30-40 ng/ml, 40-50 ng/ml, 50-60 ng/ml, 60-70 ng/ml, 70-80 ng/ml, 80-90 ng/ml, 90-100 ng/ml, 100-200 ng/ml, 200-300 ng/ml, 300-400 ng/ml and 400-500 ng/ml. The preferred concentration of BMP4 that is added to the cells is about 50 ng/ml. The duration of BMP4 exposure used in the examples is five days. However, this may be changed to four, six, or seven days.

In the third step, the hepatic differentiation factors aFGF, FGF4 and FGF8b are added to the cells.

The concentration of aFGF that is added to the cells can range from about 5 ng/ml to about 500 ng/ml. However, the invention also encompasses sub-ranges of concentrations of aFGF. For example, from about 5-10 ng/ml, 10-20 ng/ml, 20-30 ng/ml, 30-40 ng/ml, 40-50 ng/ml, 50-60 ng/ml, 60-70 ng/ml, 70-80 ng/ml, 80-90 ng/ml, 90-100 ng/ml, 100-200 ng/ml, 200-300 ng/ml, 300-400 ng/ml and 400-500 ng/ml. The preferred concentration of aFGF that is added to the cells is about 50 ng/ml. The duration of aFGF exposure used in the examples is five days. However, this may be changed to four, six, or seven days.

The concentration of FGF4 that is added to the cells can range from about 1 ng/ml to about 100 ng/ml. However, the invention also encompasses sub-ranges of concentrations of FGF4. For example, from about 1-2 ng/ml, 2-4 ng/ml, 4-6 ng/ml, 6-8 ng/ml, 8-10 ng/ml, 10-20 ng/ml, 20-30 ng/ml, 30-40 ng/ml, 40-60 ng/ml, 60-80 ng/ml and 80-100 ng/ml. The preferred concentration of FGF4 that is added to the cells is about 10 ng/ml. The duration of FGF4 exposure used in the examples is five days. However, this may be changed to four, six, or seven days.

The concentration of FGF8b that is added to the cells can range from about 2.5 ng/ml to about 250 ng/ml. However, the invention also encompasses sub-ranges of concentrations of FGF8b. For example, from about 2.5-5 ng/ml, 5-10 ng/ml, 10-15 ng/ml, 15-20 ng/ml, 20-25 ng/ml, 25-30 ng/ml, 35-40 ng/ml, 45-50 ng/ml, 50-100 ng/ml, 100-150 ng/ml, 150-200 ng/ml and 200-250 ng/ml. The preferred concentration of FGF8b that is added to the cells is about 25 ng/ml. The duration of FGF8b exposure used in the examples is five days. However, this may be changed to four, six, or seven days.

In the fourth step, the hepatic differentiation factors HGF and Follistatin are added to the cells.

The concentration of HGF that is added to the cells can range from about 2 ng/ml to about 200 ng/ml. However, the invention also encompasses sub-ranges of concentrations of HGF. For example, from about 2-5 ng/ml, 5-10 ng/ml, 10-15 ng/ml, 15-20 ng/ml, 20-25 ng/ml, 25-30 ng/ml, 30-35 ng/ml, 35-40 ng/ml, 40-50 ng/ml, 50-100 ng/ml, 100-150 ng/ml and 150-200 ng/ml. The preferred concentration of HGF that is added to the cells is about 20 ng/ml. The duration of HGF exposure used in the examples is five days. However, this may be changed to four, six, or seven days and can be as high as 30 days.

The concentration of Follistatin that is added to the cells can range from about 10 ng/ml to about 1000 ng/ml. However, the invention also encompasses sub-ranges of concentrations of Follistatin. For example, from about 10-25 ng/ml, 25-50 ng/ml, 50-75 ng/ml, 75-100 ng/ml, 100-125 ng/ml, 125-150 ng/ml, 150-175 ng/ml, 150-175 ng/ml, 175-200 ng/ml, 200-400 ng/ml, 400-600 ng/ml, 600-800 ng/ml and 800-1000 ng/ml. The preferred concentration of Follistatin that is added to the cells is about 100 ng/ml. The duration of Follistatin exposure used in the examples is five days. However, this may be changed to four, six, or seven days and can be as high as 30 days.

In another embodiment of the invention, only BMP4 (no bFGF) is used in the second step, i.e., the step after the cells are exposed to Activin-A and Wnt3a. Also in this method, the third step is not required, i.e., incubation of cells from the second step with aFGF, FGF4, or FGF8. Instead, in the third step, cells are incubated with HGF and Follistatin. Accordingly, the second step may be extended from around day 6 to around day 13. Then, the last step can be extended from day 14 through day 21 or longer, such as day 28. In addition, this may be conducted in serum-free medium, although serum could be used as well, depending upon the particular cell type.

Cells with a hepatic stellate phenotype and cells with a hepatic endothelial sinusoidal phenotype begin to be produced in the first step of the method when the pluripotent cells are incubated with a combination of activinA and Wnt3a. Accordingly, such cells can be isolated after this or after any of the following steps. However, as exemplified by human embryonic stem cells in the Examples below, the genes indicating these two phenotypes reaches a peak at about day 21. Accordingly, these cells may also be isolated at later stages in the differentiation protocol, such as on days 21-28 or longer.

Stem Cells

The present invention can be practiced, preferably, using stem cells of vertebrate species, such as humans, non-human primates, domestic animals, livestock, and other non-human mammals.

Embryonic

Stem cells have been identified in most tissues. The most well studied stem cell is the embryonic stem cell (ESC), as it has unlimited self-renewal and multipotent differentiation potential. These cells are derived from the inner cell mass of the blastocyst or can be derived from the primordial germ cells of a post-implantation embryo (embryonal germ cells or EG cells). ES and EG cells have been derived, first from mouse, and later, from many different animals, and more recently, from non-human primates and humans. When introduced into mouse blastocysts or blastocysts of other animals, ESCs can contribute to all tissues of the animal. ES and EG cells can be identified by positive staining with antibodies against SSEA1 (mouse) and SSEA4 (human). See, for example, U.S. Pat. Nos. 5,453,357; 5,656,479; 5,670,372; 5,843,780; 5,874,301; 5,914,268; 6,110,739 6,190,910; 6,200,806; 6,432,711; 6,436,701, 6,500,668; 6,703,279; 6,875,607; 7,029,913; 7,112,437; 7,145,057; 7,153,684; and 7,294,508, each of which is incorporated by reference herein for teaching ESCs and methods of making and expanding ESCs. Accordingly, ESCs and methods for isolating and expanding ESCs are well-known in the art.

A number of transcription factors and exogenous cytokines have been identified that influence the potency status of embryonic stem cells in vivo. The first transcription factor to be described that is involved in stem cell pluripotency is Oct4. Oct4 belongs to the POU (Pit-Oct-Unc) family of transcription factors and is a DNA binding protein that is able to activate the transcription of genes, containing an octameric sequence called "the octamer motif" within the promotor or enhancer region. Oct4 is expressed at the moment of the cleavage stage of the fertilized zygote until the egg cylinder is formed. The function of Oct3/4 is to repress differentiation inducing genes (i.e., FoxaD3, hCG) and to activate genes promoting pluripotency (FGF4, Utf1, Rex1). Sox2, a member of the high mobility group (HMG) box transcription factors, cooperates with Oct4 to activate transcription of genes expressed in the inner cell mass. It is essential that Oct3/4 expression in embryonic stem cells is maintained between certain levels. Overexpression or downregulation of >50% of Oct4 expression level will alter embryonic stem cell fate, with the formation of primitive endoderm/mesoderm or trophectoderm, respectively. In vivo, Oct4 deficient embryos develop to the blastocyst stage, but the inner cell mass cells are not pluripotent. Instead they differentiate along the extraembryonic trophoblast lineage. Sall4, a mammalian Spalt transcription factor, is an upstream regulator of Oct4, and is therefore important to maintain appropriate levels of Oct4 during early phases of embryology. When Sall4 levels fall below a certain threshold, trophectodermal cells will expand ectopically into the inner cell mass. Another transcription factor required for pluripotency is Nanog, named after a celtic tribe "Tir Nan Og": the land of the ever young. In vivo, Nanog is expressed from the stage of the compacted morula, is subsequently defined to the inner cell mass and is downregulated by the implantation stage. Downregulation of Nanog may be important to avoid an uncontrolled expansion of pluripotent cells and to allow multilineage differentiation during gastrulation. Nanog null embryos, isolated at day 5.5, consist of a disorganized blastocyst, mainly containing extraembryonic endoderm and no discernable epiblast.

Non-Embryonic

An example of a non-embryonic stem cell is adipose-derived adult stem cells (ADSCs) which have been isolated from fat, typically by liposuction followed by release of the ADSCs using collagenase. ADSCs are similar in many ways to MSCs derived from bone marrow, except that it is possible to isolate many more cells from fat. These cells have been reported to differentiate into bone, fat, muscle, cartilage and neurons. A method of isolation has been described in U.S. 2005/0153442.

Other non-embryonic cells reported to be capable of differentiating into cell types of more than one embryonic germ layer include, but are not limited to, cells from umbilical cord blood (see U.S. Publication No. 2002/0164794), placenta (see U.S. Publication No. 2003/0181269; umbilical cord matrix (Mitchell, K. E. et al., *Stem Cells,* 21:50-60, 2003), small embryonic-like stem cells (Kucia, M. et al., *J Physiol Pharmacol,* 57 Suppl 5:5-18, 2006), amniotic fluid stem cells (Atala, A., J Tissue Regen Med, 1:83-96, 2007), skin-derived precursors (Toma et al., *Nat Cell Biol,* 3:778-784, 2001), and bone marrow (see U.S. Publication Nos. 2003/0059414 and 2006/0147246), each of which is incorporated by reference herein for teaching these cells.

Other stem cells that are known in the art include gastrointestinal stem cells, epidermal stem cells, and hepatic stem cells, which also have been termed "oval cells" (Potten, C., et al., *Trans R Soc Lond B Biol Sci*, 353:821-830 (1998); Watt, F., *Trans R Soc Lond B Biol Sci*, 353:831 (1997); Alison et al., *Hepatology*, 29:678-683 (1998).

Strategies of Reprogramming Somatic Cells

Several different strategies such as nuclear transplantation, cellular fusion, and culture induced reprogramming have been employed to induce the conversion of differentiated cells into an embryonic state. Nuclear transfer involves the injection of a somatic nucleus into an enucleated oocyte, which, upon transfer into a surrogate mother, can give rise to a clone ("reproductive cloning"), or, upon explantation in culture, can give rise to genetically matched embryonic stem (ES) cells ("somatic cell nuclear transfer," SCNT). Cell fusion of somatic cells with ES cells results in the generation of hybrids that show all features of pluripotent ES cells. Explantation of somatic cells in culture selects for immortal cell lines that may be pluripotent or multipotent. At present, spermatogonial stem cells are the only source of pluripotent cells that can be derived from postnatal animals. Transduction of somatic cells with defined factors can initiate reprogramming to a pluripotent state. These experimental approaches have been extensively reviewed (Hochedlinger and Jaenisch, *Nature*, 441:1061-1067 (2006) and Yamanaka, S., *Cell Stem Cell*, 1:39-49 (2007)).

Nuclear Transfer

Nuclear transplantation (NT), also referred to as somatic cell nuclear transfer (SCNT), denotes the introduction of a nucleus from a donor somatic cell into an enucleated ogocyte to generate a cloned animal such as Dolly the sheep (Wilmut et al., *Nature*, 385:810-813 (1997). The generation of live animals by NT demonstrated that the epigenetic state of somatic cells, including that of terminally differentiated cells, while stable, is not irreversible fixed but can be reprogrammed to an embryonic state that is capable of directing development of a new organism. In addition to providing an exciting experimental approach for elucidating the basic epigenetic mechanisms involved in embryonic development and disease, nuclear cloning technology is of potential interest for patient-specific transplantation medicine.

Fusion of Somatic Cells and Embryonic Stem Cells

Epigenetic reprogramming of somatic nuclei to an undifferentiated state has been demonstrated in murine hybrids produced by fusion of embryonic cells with somatic cells. Hybrids between various somatic cells and embryonic carcinoma cells (Solter, D., *Nat Rev Genet*, 7:319-327 (2006), embryonic germ (EG), or ES cells (Zwaka and Thomson, *Development*, 132:227-233 (2005)) share many features with the parental embryonic cells, indicating that the pluripotent phenotype is dominant in such fusion products. As with mouse (Tada et al., *Curr Biol*, 11:1553-1558 (2001)), human ES cells have the potential to reprogram somatic nuclei after fusion (Cowan et al., *Science*, 309:1369-1373 (2005)); Yu et al., *Science*, 318:1917-1920 (2006)). Activation of silent pluripotency markers such as Oct4 or reactivation of the inactive somatic X chromosome provided molecular evidence for reprogramming of the somatic genome in the hybrid cells. It has been suggested that DNA replication is essential for the activation of pluripotency markers, which is first observed 2 days after fusion (Do and Scholer, *Stem Cells*, 22:941-949 (2004)), and that forced Overexpression of Nanog in ES cells promotes pluripotency when fused with neural stem cells (Silva et al., *Nature*, 441:997-1001 (2006)).

Culture-Induced Reprogramming

Pluripotent cells have been derived from embryonic sources such as blastomeres and the inner cell mass (ICM) of the blastocyst (ES cells), the epiblast (EpiSC cells), primordial germ cells (EG cells), and postnatal spermatogonial stem cells ("maGSCsm" "ES-like" cells). The following pluripotent cells, along with their donor cell/tissue is as follows: parthogenetic ES cells are derived from murine oocytes (Narasimha et al., *Curr Biol*, 7:881-884 (1997)); embryonic stem cells have been derived from blastomeres (Wakayama et al., *Stem Cells*, 25:986-993 (2007)); inner cell mass cells (source not applicable) (Eggan et al., *Nature*, 428:44-49 (2004)); embryonic germ and embryonal carcinoma cells have been derived from primordial germ cells (Matsui et al., *Cell*, 70:841-847 (1992)); GMCS, maSSC, and MASC have been derived from spermatogonial stem cells (Guan et al., *Nature*, 440:1199-1203 (2006); Kanatsu-Shinohara et al., *Cell*, 119:1001-1012 (2004); and Seandel et al., *Nature*, 449:346-350 (2007)); EpiSC cells are derived from epiblasts (Brons et al., *Nature*, 448:191-195 (2007); Tesar et al., *Nature*, 448:196-199(2007)); parthogenetic ES cells have been derived from human oocytes (Cibelli et al., *Science*, 295L819 (2002); Revazova et al., *Cloning Stem Cells*, 9:432-449 (2007)); human ES cells have been derived from human blastocysts (Thomson et al., *Science*, 282:1145-1147 (1998)); MAPC have been derived from bone marrow (Jiang et al., *Nature*, 418:41-49 (2002); Phinney and Prockop, *Stem Cells*, 25:2896-2902 (2007)); cord blood cells (derived from cord blood) (van de Ven et al., *Exp Hematol*, 35:1753-1765 (2007)); neurosphere derived cells derived from neural cell (Clarke et al., *Science*, 288:1660-1663 (2000)). Donor cells from the germ cell lineage such as PGCs or spermatogonial stem cells are known to be unipotent in vivo, but it has been shown that pluripotent ES-like cells (Kanatsu-Shinohara et al., *Cell*, 119:1001-1012 (2004) or maGSCs (Guan et al., *Nature*, 440:1199-1203 (2006), can be isolated after prolonged in vitro culture. While most of these pluripotent cell types were capable of in vitro differentiation and teratoma formation, only ES, EG, EC, and the spermatogonial stem cell-derived maGCSs or ES-like cells were pluripotent by more stringent criteria, as they were able to form postnatal chimeras and contribute to the germline Recently, multipotent adult spermatogonial stem cells (MASCs) were derived from testicular spermatogonial stem cells of adult mice, and these cells had an expression profile different from that of ES cells (Seandel et al., *Nature*, 449:346-350 (2007)) but similar to EpiSC cells, which were derived from the epiblast of postimplantation mouse embryos (Brons et al., *Nature*, 448:191-195 (2007); Tesar et al., *Nature*, 448:196-199 (2007)).

Reprogramming by Defined Transcription Factors

Figure 2A:
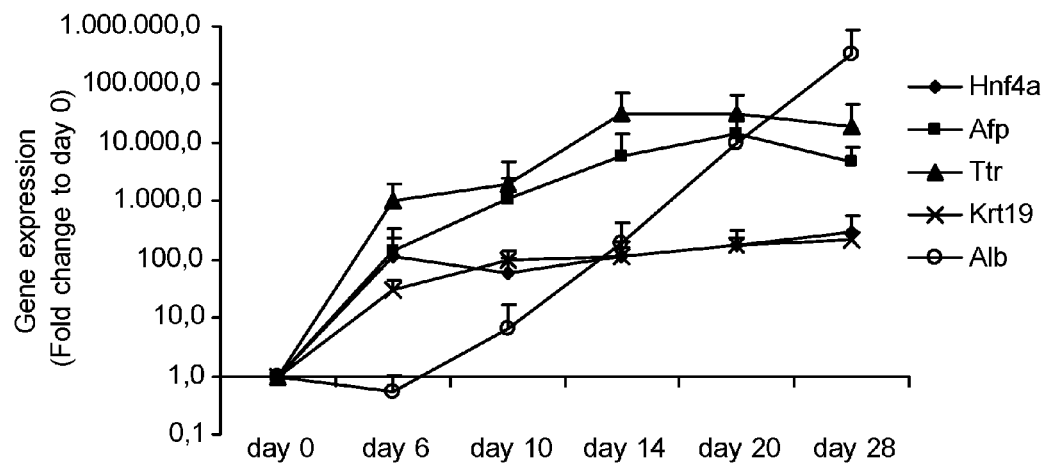
FIGS. 2A and 2B. Gene expression analysis (hepatocytes) at different steps of the differentiation and comparison to mature hepatocytes. Gene expression analysis by real-time RT-PCR at day 0, day 6, day 10, day 14, day 20, and day 28 of the differentiation of the iPS cell line J3. Key genes expressed in (A) hepatoblasts and immature hepatocytes and (B) mature hepatocytes. Results are shown as mean ($2^{-\Delta\Delta C_t}$) fold change respect to day 0±standard deviation of three independent differentiations.

Takahashi and Yamanaka have reported reprogramming somatic cells back to an ES-like state (Takahashi and Yamanaka, *Cell*, 126:663-676 (2006)). They successfully reprogrammed mouse embryonic fibroblasts (MEFs) and adult fibroblasts to pluripotent ES-like cells after viral-mediated transduction of the four transcription factors Oct4, Sox2, c-myc, and Klf4 followed by selection for activation of the Oct4 target gene Fbx15 (FIG. 2A). Cells that had activated Fbx15 were coined iPS (induced pluripotent stem) cells and were shown to be pluripotent by their ability to form teratomas, although they were unable to generate live chimeras. This pluripotent state was dependent on the continuous viral expression of the transduced Oct4 and Sox2 genes, whereas the endogenous Oct4 and Nanog genes were either not expressed or were expressed at a lower level than in ES cells, and their respective promoters were found to be largely methylated. This is consistent with the conclusion that the Fbx15-iPS cells did not correspond to ES cells but may have represented an incomplete state of reprogramming. While genetic experiments had established that Oct4 and Sox2 are essential for pluripotency (Chambers and Smith, Oncogene, 23:7150-7160 (2004); Ivanona et al., Nature, 442:5330538 (2006); Masui et al., Nat Cell Biol, 9:625-635 (2007)), the role of the two oncogenes c-myc and Klf4 in reprogramming is less clear. Some of these oncogenes may, in fact, be dispensable for reprogramming, as both mouse and human iPS cells have been obtained in the absence of c-myc transduction, although with low efficiency (Nakagawa et al., Nat Biotechnol, 26:191-106 (2008); Werning et al., Nature, 448:318-324 (2008); Yu et al., Science, 318: 1917-1920 (2007)).

MAPC

Human MAPCs are described in U.S. Pat. No. 7,015,037. MAPCs have been identified in other mammals. Murine MAPCs, for example, are also described in U.S. Pat. No. 7,015,037. Rat MAPCs are also described in U.S. Pat. No. 7,838,289.

These references are incorporated by reference for describing MAPCs first isolated by Catherine Verfaillie and also for the methods used to isolate and culture the MAPCs.

Isolation and Growth of MAPCs

Methods of MAPC isolation are known in the art. See, for example, U.S. Pat. No. 7,015,037, and these methods, along with the characterization (phenotype) of MAPCs, are incorporated herein by reference. MAPCs can be isolated from multiple sources, including, but not limited to, bone marrow, placenta, umbilical cord and cord blood, muscle, brain, liver, spinal cord, blood or skin. It is, therefore, possible to obtain bone marrow aspirates, brain or liver biopsies, and other organs, and isolate the cells using positive or negative selection techniques available to those of skill in the art, relying upon the genes that are expressed (or not expressed) in these cells (e.g., by functional or morphological assays such as those disclosed in the above-referenced applications, which have been incorporated herein by reference).

MAPCs have also been obtained my modified methods described in Breyer et al., Experimental Hematology, 34:1596-1601 (2006) and Subramanian et al., Cellular Programming and Reprogramming: Methods and Protocols; S. Ding (ed.), Methods in Molecular Biology, 636:55-78 (2010), incorporated by reference for these methods.

MAPCs from Human Bone Marrow as Described in U.S. Pat. No. 7,015,037

MAPCs do not express the common leukocyte antigen CD45 or erythroblast specific glycophorin-A (Gly-A). The mixed population of cells was subjected to a Ficoll Hypaque separation. The cells were then subjected to negative selection using anti-CD45 and anti-Gly-A antibodies, depleting the population of CD45$^+$ and Gly-A$^+$ cells, and the remaining approximately 0.1% of marrow mononuclear cells were then recovered. Cells could also be plated in fibronectin-coated wells and cultured as described below for 2-4 weeks to deplete the cells of CD45$^+$ and Gly-A$^+$ cells. In cultures of adherent bone marrow cells, many adherent stromal cells undergo replicative senescence around cell doubling 30 and a more homogenous population of cells continues to expand and maintains long telomeres.

Alternatively, positive selection could be used to isolate cells via a combination of cell-specific markers. Both positive and negative selection techniques are available to those of skill in the art, and numerous monoclonal and polyclonal antibodies suitable for negative selection purposes are also available in the art (see, for example, Leukocyte Typing V, Schlossman, et al., Eds. (1995) Oxford University Press) and are commercially available from a number of sources.

Techniques for mammalian cell separation from a mixture of cell populations have also been described by Schwartz, et al., in U.S. Pat. No. 5,759,793 (magnetic separation), Basch et al., 1983 (immunoaffinity chromatography), and Wysocki and Sato, 1978 (fluorescence-activated cell sorting).

Cells may be cultured in low-serum or serum-free culture medium. Serum-free medium used to culture MAPCs is described in U.S. Pat. No. 7,015,037. Commonly-used growth factors include but are not limited to platelet-derived growth factor and epidermal growth factor. See, for example, U.S. Pat. Nos. 7,169,610; 7,109,032; 7,037,721; 6,617,161; 6,617,159; 6,372,210; 6,224,860; 6,037,174; 5,908,782; 5,766,951; 5,397,706; and 4,657,866; all incorporated by reference for teaching growing cells in serum-free medium.

Additional Culture Methods

In additional experiments the density at which MAPCs are cultured can vary from about 100 cells/cm$^2$ or about 150 cells/cm$^2$ to about 10,000 cells/cm$^2$, including about 200 cells/cm$^2$ to about 1500 cells/cm$^2$ to about 2000 cells/cm$^2$. The density can vary between species. Additionally, optimal density can vary depending on culture conditions and source of cells. It is within the skill of the ordinary artisan to determine the optimal density for a given set of culture conditions and cells.

Also, effective atmospheric oxygen concentrations of less than about 10%, including about 1-5% and, especially, 3-5%, can be used at any time during the isolation, growth and differentiation of MAPCs in culture.

Cells may be cultured under various serum concentrations, e.g., about 2-20%. Fetal bovine serum may be used. Higher serum may be used in combination with lower oxygen tensions, for example, about 15-20%. Cells need not be selected prior to adherence to culture dishes. For example, after a Ficoll gradient, cells can be directly plated, e.g., 250,000-500,000/cm$^2$. Adherent colonies can be picked, possibly pooled, and expanded.

In one embodiment, used in the experimental procedures in the Examples, high serum (around 15-20%) and low oxygen (around 3-5%) conditions were used for the cell culture. Specifically, adherent cells from colonies were plated and passaged at densities of about 1700-2300 cells/cm$^2$ in 18% serum and 3% oxygen (with PDGF and EGF).

In an embodiment specific for MAPCs, supplements are cellular factors or components that allow MAPCs to retain the ability to differentiate into all three lineages. This may be indicated by the expression of specific markers of the undifferentiated state. MAPCs, for example, constitutively express Oct 3/4 (Oct 3A) and maintain high levels of telomerase.

Cell Culture

In general, cells useful for the invention can be maintained and expanded in culture medium that is available to and well-known in the art. Such media include, but are not limited to, Dulbecco's Modified Eagle's Medium® (DMEM), DMEM F12 medium®, Eagle's Minimum Essential Medium®, F-12K medium®, Iscove's Modified Dulbecco's Medium® and RPMI-1640 medium®. Many media are also available as low-glucose formulations, with or without sodium pyruvate.

Also contemplated in the present invention is supplementation of cell culture medium with mammalian sera. Sera often contain cellular factors and components that are necessary for viability and expansion. Examples of sera include fetal bovine serum (FBS), bovine serum (BS), calf serum (CS), fetal calf serum (FCS), newborn calf serum (NCS), goat serum (GS), horse serum (HS), human serum, chicken serum, porcine serum, sheep serum, rabbit serum, serum replacements and bovine embryonic fluid. It is understood that sera can be heat-inactivated at 55-65° C. if deemed necessary to inactivate components of the complement cascade.

Additional supplements also can be used advantageously to supply the cells with the necessary trace elements for optimal growth and expansion. Such supplements include insulin, transferrin, sodium selenium and combinations thereof. These components can be included in a salt solution such as, but not limited to, Hanks' Balanced Salt Solution® (HBSS), Earle's Salt Solution®, antioxidant supplements, MCDB-201® supplements, phosphate buffered saline (PBS), ascorbic acid and ascorbic acid-2-phosphate, as well as additional amino acids. Many cell culture media already contain amino acids, however, some require supplementation prior to culturing cells. Such amino acids include, but are not limited to, L-alanine, L-arginine, L-aspartic acid, L-asparagine, L-cysteine, L-cystine, L-glutamic acid, L-glutamine, L-glycine, L-histidine, L-isoleucine, L-leucine, L-lysine, L-methionine, L-phenylalanine, L-proline, L-serine, L-threonine, L-tryptophan, L-tyrosine, and L-valine. It is well within the skill of one in the art to determine the proper concentrations of these supplements.

Hormones also can be advantageously used in the cell cultures of the present invention and include, but are not limited to, D-aldosterone, diethylstilbestrol (DES), dexamethasone, β-estradiol, hydrocortisone, insulin, prolactin, progesterone, somatostatin/human growth hormone (HGH), thyrotropin, thyroxine and L-thyronine.

Lipids and lipid carriers also can be used to supplement cell culture media, depending on the type of cell and the fate of the differentiated cell. Such lipids and carriers can include, but are not limited to, cyclodextrin (α, β, γ), cholesterol, linoleic acid conjugated to albumin, linoleic acid and oleic acid conjugated to albumin, unconjugated linoleic acid, linoleic-oleic-arachidonic acid conjugated to albumin and oleic acid unconjugated and conjugated to albumin, among others.

Cells may be cultured in low-serum or serum-free culture medium. Serum-free medium used to culture MAPCs is described in U.S. Pat. No. 7,015,037. Many cells have been grown in serum-free or low-serum medium. In this case, the medium is supplemented with one or more growth factors. Commonly used growth factors include, but are not limited to, bone morphogenic protein, basis fibroblast growth factor, platelet-derived growth factor and epidermal growth factor. See, for example, U.S. Pat. Nos. 7,169,610; 7,109,032; 7,037,721; 6,617,161; 6,617,159; 6,372,210; 6,224,860; 6,037,174; 5,908,782; 5,766,951; 5,397,706; and 4,657,866; all incorporated by reference herein for teaching growing cells in serum-free medium.

Cells may also be grown in "3D" (aggregated) cultures. An example is PCT/US09/31528; filed Jan. 21, 2009.

Once established in culture, cells can be used fresh or frozen and stored as frozen stocks, using, for example, DMEM with 40% FCS and 10% DMSO. Other methods for preparing frozen stocks for cultured cells also are available to those skilled in the art.

Methods of identifying and subsequently separating differentiated cells from their undifferentiated counterparts can be carried out by methods well known in the art. Cells that have been induced to differentiate using methods of the present invention can be identified by selectively culturing cells under conditions whereby differentiated cells outnumber undifferentiated cells. Similarly, differentiated cells can be identified by morphological changes and characteristics that are not present on their undifferentiated counterparts, such as cell size and the complexity of intracellular organelle distribution. Also contemplated are methods of identifying differentiated cells by their expression of specific cell-surface markers such as cellular receptors and transmembrane proteins. Monoclonal antibodies against these cell-surface markers can be used to identify differentiated cells. Detection of these cells can be achieved through fluorescence activated cell sorting (FACS) and enzyme-linked immunosorbent assay (ELISA). From the standpoint of transcriptional upregulation of specific genes, differentiated cells often display levels of gene expression that are different from undifferentiated cells. Reverse-transcription polymerase chain reaction, or RT-PCR, also can be used to monitor changes in gene expression in response to differentiation. Whole genome analysis using microarray technology also can be used to identify differentiated cells.

Accordingly, once differentiated cells are identified, they can be separated from their undifferentiated counterparts, if necessary. The methods of identification detailed above also provide methods of separation, such as FACS, preferential cell culture methods, ELISA, magnetic beads and combinations thereof. One embodiment of the present invention contemplates the use of FACS to identify and separate cells based on cell-surface antigen expression.

Pharmaceutical Formulations

Any of the cells produced by the methods described herein can be used in the clinic to treat a subject. They can, therefore, be formulated into a pharmaceutical composition. Therefore, in certain embodiments, the isolated or purified cell populations are present within a composition adapted for and suitable for delivery, i.e., physiologically compatible. Accordingly, compositions of the cell populations will often further comprise one or more buffers (e.g., neutral buffered saline or phosphate buffered saline), carbohydrates (e.g., glucose, mannose, sucrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives.

In other embodiments, the isolated or purified cell populations are present within a composition adapted for or suitable for freezing or storage.

In many embodiments the purity of the cells for administration to a subject is about 100%. In other embodiments it is 95% to 100%. In some embodiments it is 85% to 95%. Particularly in the case of admixtures with other cells, the percentage can be about 10%-15%, 15%-20%, 20%-25%, 25%-30%, 30%-35%, 35%-40%, 40%-45%, 45%-50%, 60%-70%, 70%-80%, 80%-90%, or 90%-95%. Or isolation/purity can be expressed in terms of cell doublings where the cells have undergone, for example, 10-20, 20-30, 30-40, 40-50 or more cell doublings.

The numbers of cells in a given volume can be determined by well known and routine procedures and instrumentation. The percentage of the cells in a given volume of a mixture of cells can be determined by much the same procedures. Cells can be readily counted manually or by using an automatic cell counter. Specific cells can be determined in a given volume using specific staining and visual examination and by automated methods using specific binding reagent, typically antibodies, fluorescent tags, and a fluorescence activated cell sorter.

The choice of formulation for administering the cells for a given application will depend on a variety of factors. Prominent among these will be the species of subject, the nature of the disorder, dysfunction, or disease being treated and its state and distribution in the subject, the nature of other therapies and agents that are being administered, the optimum route for administration, survivability via the route, the dosing regimen, and other factors that will be apparent to those skilled in the art. In particular, for instance, the choice of suitable carriers and other additives will depend on the exact route of administration and the nature of the particular dosage form.

Final formulations of the aqueous suspension of cells/medium will typically involve adjusting the ionic strength of the suspension to isotonicity (i.e., about 0.1 to 0.2) and to physiological pH (i.e., about pH 6.8 to 7.5). The final formulation will also typically contain a fluid lubricant, such as maltose, which must be tolerated by the body. Exemplary lubricant components include glycerol, glycogen, maltose and the like. Organic polymer base materials, such as polyethylene glycol and hyaluronic acid as well as non-fibrillar collagen, preferably succinylated collagen, can also act as lubricants. Such lubricants are generally used to improve the injectability, intrudability and dispersion of the injected biomaterial at the site of injection and to decrease the amount of spiking by modifying the viscosity of the compositions. This final formulation is by definition the cells in a pharmaceutically acceptable carrier.

The cells are subsequently placed in a syringe or other injection apparatus for precise placement at the site of the tissue defect. The term "injectable" means the formulation can be dispensed from syringes having a gauge as low as 25 under normal conditions under normal pressure without substantial spiking. Spiking can cause the composition to ooze from the syringe rather than be injected into the tissue. For this precise placement, needles as fine as 27 gauge (200µ I.D.) or even 30 gauge (150µ I.D.) are desirable. The maximum particle size that can be extruded through such needles will be a complex function of at least the following: particle maximum dimension, particle aspect ratio (length:width), particle rigidity, surface roughness of particles and related factors affecting particle:particle adhesion, the viscoelastic properties of the suspending fluid, and the rate of flow through the needle. Rigid spherical beads suspended in a Newtonian fluid represent the simplest case, while fibrous or branched particles in a viscoelastic fluid are likely to be more complex.

The desired isotonicity of the compositions of this invention may be accomplished using sodium chloride, or other pharmaceutically acceptable agents such as dextrose, boric acid, sodium tartrate, propylene glycol, or other inorganic or organic solutes. Sodium chloride is preferred particularly for buffers containing sodium ions.

A pharmaceutically acceptable preservative or stabilizer can be employed to increase the life of cell/medium compositions. If such preservatives are included, it is well within the purview of the skilled artisan to select compositions that will not affect the viability or efficacy of the cells.

Those skilled in the art will recognize that the components of the compositions should be chemically inert. This will present no problem to those skilled in chemical and pharmaceutical principles. Problems can be readily avoided by reference to standard texts or by simple experiments (not involving undue experimentation) using information provided by the disclosure, the documents cited herein, and generally available in the art.

Sterile injectable solutions can be prepared by incorporating the cells/medium utilized in practicing the present invention in the required amount of the appropriate solvent with various amounts of the other ingredients, as desired.

In some embodiments, cells/medium are formulated in a unit dosage injectable form, such as a solution, suspension, or emulsion. Pharmaceutical formulations suitable for injection of cells/medium typically are sterile aqueous solutions and dispersions. Carriers for injectable formulations can be a solvent or dispersing medium containing, for example, water, saline, phosphate buffered saline, polyol (for example, glycerol, propylene glycol, liquid polyethylene glycol, and the like), and suitable mixtures thereof.

In the case of treating liver deficiency, in particular, the cells may be enclosed in a device that can be implanted in a subject. Cells can be implanted in or near the liver or elsewhere to replace or supplement liver function. Cells can also be implanted without being in a device, e.g., in existing liver tissue.

Dosing

Compositions can be administered in dosages and by techniques well known to those skilled in the medical and veterinary arts taking into consideration such factors as the age, sex, weight, and condition of the particular patient, and the formulation that will be administered (e.g., solid vs. liquid). Doses for humans or other mammals can be determined without undue experimentation by the skilled artisan, from this disclosure, the documents cited herein, and the knowledge in the art.

The dose of cells/medium appropriate to be used in accordance with various embodiments of the invention will depend on numerous factors. It may vary considerably for different circumstances. The parameters that will determine optimal doses to be administered for primary and adjunctive therapy generally will include some or all of the following: the disease being treated and its stage; the species of the subject, their health, gender, age, weight, and metabolic rate; the subject's immunocompetence; other therapies being administered; and expected potential complications from the subject's history or genotype. The parameters may also include: whether the cells are syngeneic, autologous, allogeneic, or xenogeneic; their potency (specific activity); the site and/or distribution that must be targeted for the cells/medium to be effective; and such characteristics of the site such as accessibility to cells/medium and/or engraftment of cells. Additional parameters include co-administration with other factors (such as growth factors and cytokines). The optimal dose in a given situation also will take into consideration the way in which the cells/medium are formulated, the way they are administered, and the degree to which the cells/medium will be localized at the target sites following administration. Finally, the determination of optimal dosing necessarily will provide an effective dose that is neither below the threshold of maximal beneficial effect nor above the threshold where the deleterious effects associated with the dose outweighs the advantages of the increased dose.

The optimal dose of cells for some embodiments will be in the range of doses used for autologous, mononuclear bone marrow transplantation. For fairly pure preparations of cells, optimal doses in various embodiments will range from $10^4$ to $10^8$ cells/kg of recipient mass per administration. In some embodiments the optimal dose per administration will be between $10^5$ to $10^7$ cells/kg. In many embodiments the optimal dose per administration will be $5 \times 10^5$ to $5 \times 10^6$ cells/kg. By way of reference, higher doses in the foregoing are analogous to the doses of nucleated cells used in autologous mononuclear bone marrow transplantation. Some of the lower doses are analogous to the number of CD34+ cells/kg used in autologous mononuclear bone marrow transplantation.

It is to be appreciated that a single dose may be delivered all at once, fractionally, or continuously over a period of time. The entire dose also may be delivered to a single location or spread fractionally over several locations.

In various embodiments, cells/medium may be administered in an initial dose, and thereafter maintained by further administration. Cells/medium may be administered by one method initially, and thereafter administered by the same method or one or more different methods. The levels can be maintained by the ongoing administration of the cells/medium. Various embodiments administer the cells/medium either initially or to maintain their level in the subject or both by intravenous injection. In a variety of embodiments, other forms of administration, are used, dependent upon the patient's condition and other factors, discussed elsewhere herein.

It is noted that human subjects are treated generally longer than experimental animals; but, treatment generally has a length proportional to the length of the disease process and the effectiveness of the treatment. Those skilled in the art will take this into account in using the results of other procedures carried out in humans and/or in animals, such as rats, mice, non-human primates, and the like, to determine appropriate doses for humans. Such determinations, based on these considerations and taking into account guidance provided by the present disclosure and the prior art will enable the skilled artisan to do so without undue experimentation.

Suitable regimens for initial administration and further doses or for sequential administrations may all be the same or may be variable. Appropriate regimens can be ascertained by the skilled artisan, from this disclosure, the documents cited herein, and the knowledge in the art.

The dose, frequency, and duration of treatment will depend on many factors, including the nature of the disease, the subject, and other therapies that may be administered. Accordingly, a wide variety of regimens may be used to administer the cells/medium.

In some embodiments, cells/medium are administered to a subject in one dose. In others cells/medium are administered to a subject in a series of two or more doses in succession. In some other embodiments wherein cells/medium are administered in a single dose, in two doses, and/or more than two doses, the doses may be the same or different, and they are administered with equal or with unequal intervals between them.

Cells/medium may be administered in many frequencies over a wide range of times. In some embodiments, they are administered over a period of less than one day. In other embodiment they are administered over two, three, four, five, or six days. In some embodiments they are administered one or more times per week, over a period of weeks. In other embodiments they are administered over a period of weeks for one to several months. In various embodiments they may be administered over a period of months. In others they may be administered over a period of one or more years. Generally lengths of treatment will be proportional to the length of the disease process, the effectiveness of the therapies being applied, and the condition and response of the subject being treated.

Uses for the Cells (1) Therapy of Liver Failure:

The invention is directed to methods of treating liver deficiencies by administering the cells of the invention to a subject with the liver deficiency. Such deficiencies include, but are not limited to, toxic liver disease, metabolic liver disease, acute liver necrosis, effects of acetaminophen, hemochromatosis, Wilson's Disease, Crigler Najar, hereditary tyrosinemia, familial intrahepatic cholestatis type 3, ornithine transcarbamylase (OTC) deficiency, and urea cycle disorder.

Further diseases include, but are not limited to viral hepatitis, chronic viral hepatitis A, B, C, acute hepatitis A, B, C, D, E, cytomegalovirus and herpes simplex virus; liver dysfunction in other infectious diseases such as, without limitation, toxoplasmosis, hepatosplenic schistosomiasis, liver disease in syphilis, leptospirosis and amoebiasis; metabolic diseases such as, without limitation, haemochromatosis, Gilbert's syndrome, Dubin-Johnson syndrome and Rotor's syndrome; alcoholic liver disease such as, without limitation, fatty liver, fibrosis, sclerosis and cirrhosis; and toxic liver disease.

(2) Bioartificial Liver (BAL) Devices

In patients with terminal liver failure, the use of bioartificial liver devices has been proposed to bridge the time to liver transplantation (ref). BAL devices are designed to support the detoxification functions performed by the liver, hence decreasing the risk and severity of CNS complications associated with acute liver failure. BAL devices could benefit three groups of patients; those with fulminant hepatic failure, those waiting for an imminent transplant, and those with early failure of a liver transplant. Although some positive results have been seen in patients with liver failure, further exploration of the usefulness of BAL devices has been hampered by lack of suitable cells. Currently, tumor-derived cell lines or animal cells, which might be associated with possible tumor cell seeding, immune responses, and xeno-zoonoses, are used. The availability of cells with full mature hepatic function of human origin, would enable investigators to further test and optimize BAL devices to bridge patients till the liver spontaneously regenerates or a donor-liver is available. Although clinical trials have in general not been successful, some encouraging results have been seen in patients with acute liver failure. Accordingly, the cells of the invention can be used in such bioartificial liver devices.

(3) Pharmaceutical Testing

As discussed in the background of this application, the quiescent hepatic stellate cells are the chief cells responsible for liver fibrosis. A renewable source of these cells, therefore, is highly desirable for discovering compounds that may be effective in an anti-fibrotic therapy. The anti-fibrotic therapies must be inhibiting the activation of the hepatic stellate cells. This is responsible for the fibrotic response to injury. Accordingly, the quiescent hepatic stellate cells produced by the methods described in this application can be used to screen for compounds that inhibit/prevent stellate cell activation and, therefore, are potential candidates for treatment and prevention of liver fibrosis.

Drug discovery involves screening one or more compounds for the ability to modulate the function or phenotype of the HSCs or LSECs. Accordingly, the assay may be designed to be conducted in vivo or in vitro.

One could directly assay protein or RNA. This can be done through any of the well-known techniques available in the art, such as by FACS and other antibody-based detection methods and PCR and other hybridization-based detection methods. One could also perform biological assays for one or more biological effects of the agent to be tested.

Assays for expression/secretion include, but are not limited to, ELISA, Luminex qRT-PCR, anti-factor western blots, and factor immunohistochemistry.

Agents can be discovered through screening the cells with large combinatorial libraries. These compound libraries may be libraries of agents that include, but are not limited to, small organic molecules, antisense nucleic acids, siRNA DNA aptamers, peptides, antibodies, non-antibody proteins, cytokines, chemokines, and chemo-attractants.

The present invention is additionally described by way of the following illustrative, non-limiting Example that provides a better understanding of the present invention and of its many advantages.

EXAMPLES

Example 1

Directed Differentiation of Murine Induced Pluripotent Stem Cells to Cells Having Hepatocyte, Hepatic Stellate, and Hepatic Sinusoidal Endothelial Phenotype Induced pluripotent stem (iPS) cells exert phenotypic and functional characteristics of embryonic stem cells. It is useful to develop differentiation procedures to induce iPS cell differentiation. This Example describes the differentiation of mouse iPS cells to hepatocyte-like cells in vitro using a differentiation procedure. By sequential stimulation with cytokines known to play a role in liver development, iPS cells were specified to primitive streak/mesendoderm/definitive endoderm, followed by differentiation to cells with hepatoblast features, and some cells with differentiated hepatocyte-like functional properties, such as albumin secretion, glycogen storage, urea production and inducible cytochrome activity.

In addition to hepatocyte-like cells, mesodermal cells with characteristics of liver sinusoidal endothelium and stellate cells were also produced.

Introduction

The generation of induced pluripotent stem (iPS) cells from terminally differentiated adult cell types has been described (Takahashi et al., *Cell.* 131:861-72. (2007); Takahashi et al., *Cell* 126:663-76 (2006); Liao et al., *Cell Stem Cell;* 4:11-5 (2009); Li et al., *Cell Stem Cell* 4:16-9 (2009)). IPS cells were initially generated by using viral vectors of specific transcription factors that turn on the transcriptional regulatory circuit of pluripotent cells. More recently, iPS cells have also been generated by non-integrating methods alone or in combination with small molecules that affect methylation or acetylation, mimic the Wnt signalling pathway or modulate the transforming growth factor (TGF)β pathway (Li et al., *Cell Stem Cell* 4:16-9 (2009); Okita et al., *Science* 322:949-53 (2008); and Feng et al., *Cell Stem Cell* 4:301-12 (2009)). The possibility to generate pluripotent cells from any kind of adult cell has raised the possibility to create patient-specific cells that are immunologically compatible with the host for cell therapy approaches. It also opens the possibility to easily create disease models to investigate the role of particular genes in liver development (Colman et al., *Cell Stem Cell* 5:244-7 (2009)). Differentiation of iPS cells to hepatocyte-like cells has been recently described (Song et al., *Cell Res* 19:1233-11242 (2009); Gai et al., *Differentiation* 79:171-181 (2010)).

This Example describes the differentiation of mouse iPS cells to functional hepatocyte-like cells following a hepatocyte differentiation protocol that mimics embryonic liver development by inducing the differentiation of pluripotent cells to form definitive endoderm, hepatoblasts and hepatocyte-like cells. The procedure also results in cells having a hepatic stellate and hepatic sinusoidal endothelial phenotype.

Methods

IPS cell generation. IPS cells were generated using the protocol described by Takahashi et al. (*Nat Protoc* 2:3081-9 (2007)), from the adherent fraction of the bone marrow (iPS lines J3 and J23) from Oct4-GFP mice (Lengner et al., *Cell Stem Cell* 1:403-15 (2007)), and from tail clip fibroblasts (iPS line A1) form Tg(Pou5f1-EGFP)2Mnn (CBA/CaJxC57BL/6J) mice. Briefly, bone marrow adherent cells were cultured in differentiation medium supplemented with 10 ng/ml mouse epidermal growth factor, 10 ng/ml human platelet derived growth factor-ββ, 1000 units/ml murine Leukemia Inhibitory Factor (mLIF) and 2% fetal bovine serum (FBS). Tail clip was obtained from Oct4-GFP mice, minced and cultured on gelatin coated plated in fibroblast expansion medium: high glucose Dulbecco's Modified Eagle Medium (DMEM), 10% FBS (Hyclone), and 1% L-Glutamine Cells that grew out of the tissue were cultured and expanded until transduced with retrovirus.

Retroviruses were produced with VSV-G envelope. pMX vectors carried Sox2, Oct4, c-Myc and Klf4. $8\times10^5$ cells were infected in the presence of polybrene (4 µG/mL final), with 2:1:1:1 ratio of Sox2, Oct4, c-Myc and Klf4 viruses respectively. Cells were transduced in DMEM containing 10% FBS. On the following day, the medium was changed to ESC medium containing high glucose DMEM containing 16% FBS, 1% L-Glutamine, 1x non essential amino acids, 1 mM sodium pyruvate, 100 µM β-mercaptoethanol, 1000 units/ml mLIF. Medium was changed daily. Once ESC-like colonies appeared, they were handpicked and propagated on mouse embryonic fibroblasts (MEF) feeders. iPS characterization was performed by analyzing the expression of Rex1, Ecat1, Fbx15, Dppa4, Dppa5, Tdgf1, Utf1, Gdf3, Essrb and Nanog, teratoma formation and in vitro direct differentiation to neurectoderm, mesoderm and endoderm fate.

Transgene expression of Sox2, Oct4, c-Myc and Klf4 was silenced in established cell lines and no reactivation was observed during differentiation. iPS cell lines were used between passage 7 and 15.

Mouse iPS differentiation. Prior to starting the hepatic differentiation, undifferentiated iPS cells were plated for one passage on gelatin without MEFs in ESC medium. To start the hepatocyte differentiation protocol, mouse iPS cells were plated in 12 well plates, pre-coated with 2% matrigel diluted in PBS for 1-2 hours at 37° C., just before plating the cells. Cells were seeded at 2500 cells/cm$^2$ in differentiation medium (day 0). Differentiation medium consisted of 60% DMEM, low glucose, 40% MCDB-201-water, 0.25× Linoleic acid-Bovine serum albumin, 0.25× Insulin-transferrin-selenium, $10^{-4}$M L-Ascorbic Acid, $1\times10^{-6}$M Dexamethasone, 100 µM 2-mercaptoethanol. Plates were kept at 21% $O_2$ and 5.8% $CO_2$ in a humidified incubator during the differentiation. Media was changed 70% every other day and completely when the medium components were changed (d6, d10, d14). 2% FBS was added on day 0-2 and 0.5% FBS from day 3 to 28. Cytokines were added as follows: Activin A (100 ng/ml) and Wnt3a (50 ng/ml) from day 0 to day 6, bone morphogenetic protein (BMP)4 (50 ng/ml) FGF2 (10 ng/ml) from day 7 to day 10, acidic (a) FGF (50 ng/ml), FGF4 (l0 ng/ml) and FGF8b (25 ng/ml) from dl 1 to day 14, and from day 15 to day 28 hepatocyte growth factor (HGF) (20 ng/ml) and follistatin (100 ng/ml). A diagram of the differentiation protocol can be found in FIG. 1A.

Gene expression analysis. RNA isolation and DNase treatment was performed by the RNeasy Micro-kit (Qiagen 74004). cDNA was synthesised from 1 µg of RNA with Superscript III First-Strand synthesis system (Invitrogen 18080-051). Real time PCR was performed with Platinum SYBR Green qPCR Supermix-UDG (Invitrogen 11733-046) in an Eppendorf realplex (Eppendorf) equipment. In FIGS. 1 and 2 results are analyzed by the $2^{(-\Delta\Delta Ct)}$ method and expressed as fold change to undifferentiated iPS. When a gene was not expressed in undifferentiated cells, a Ct value of 35 was given. In the FIGS. 12-14, results are expressed as delta Ct value with respect to Gapdh, calculated as (gene Ct value—Gapdh Ct value) are presented.

Albumin secretion. Level of mouse albumin was measured in cells supernatant using a quantitative ELISA kit (Starter Kit Bethyl E101 and ELISA kit Bethyl E90-134).

Urea production. Urea production of the cells was quantified in 24 h cell supernatants with a QuantiChrom™ Urea Assay Kit (BioAssay Systems DIUR-500).

Glycogen storage. Glycogen content was measured according to the spectrophotometric method of Seifter et al. (*Arch Biochem* 25:191-200 (1950)) miPS cell progeny was scraped and collected in 200 µl $H_2O$. 60 µl cell homogenate was mixed with 240 µl 33% KOH and incubated for 20 minutes at 100° C. 125 µl of the mixture was mixed with 875 µl $H_2O$ and 2 ml 0.2% anthrone (Sigma A-1631, 2 mg/mL 95% $H_2SO_4$). Absorbance was measured at 620 nm. A standard curve was made with glycogen (Sigma G-0885) in $H_2O$.

Cytochrome P450 activity. Cytochrome lag activity was detected by using the non-lytic method of P450-Glo™ Assay (Promega V8771). Mouse iPS cells were incubated with luminogenic substrate (Luciferin-ME) for 4 hours at 37° C. 50 µl was mixed with 50 µl Luciferin Detection Reagent in triplicate. Mean luminescence was calculated from 11 consecutive time points with 2 minutes interval. Induction of Cyp1a2 was performed by incubation with 100 µM phenobarbital.

Statistical analysis. Results are expressed as means±SEM of at least three independent experiments. Statistical analysis was performed by unpaired Student's t test, where $p<0.05$ was considered significant.

Results

Differentiation of Mouse iPS Mimics Embryonic and Fetal Liver Development

Figure 1B:
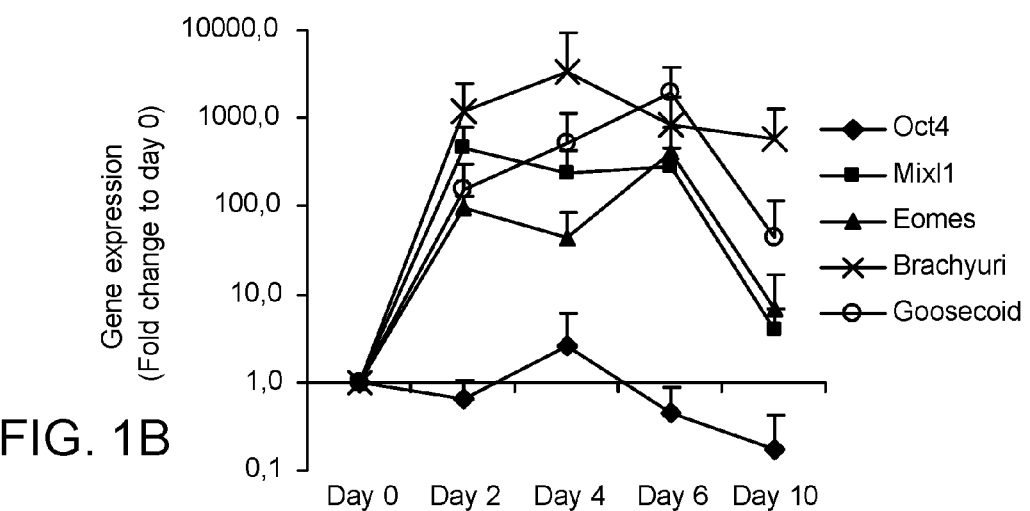
Figure 1C:
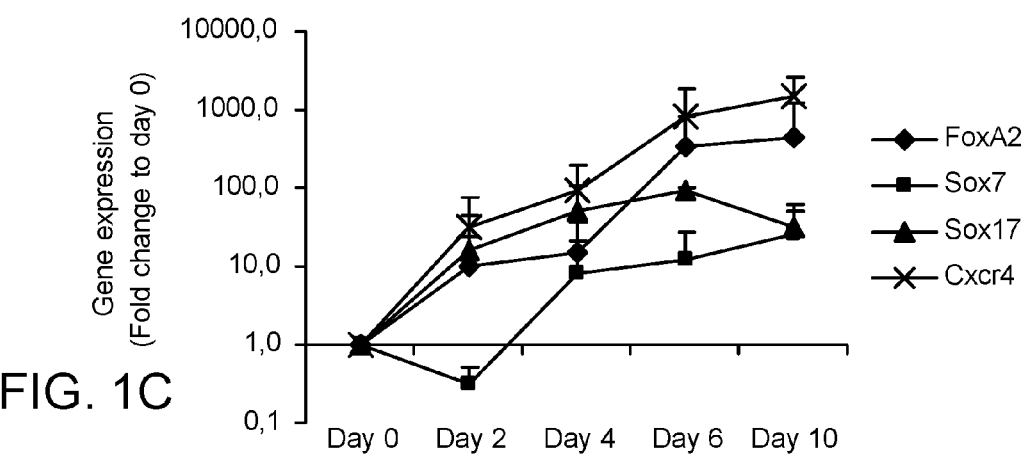
Figure 2B:
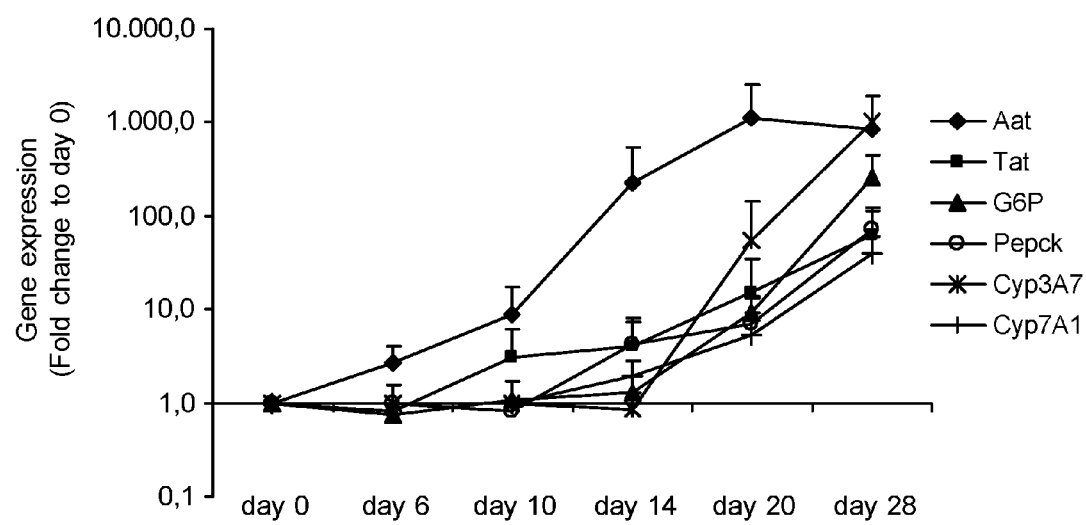
Figure 3A:
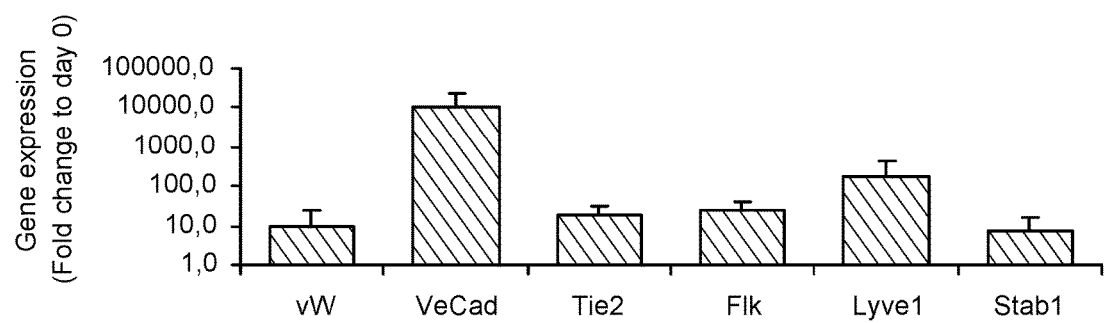
FIGS. 3A and 3B. Differentiation to mesodermal cell types (hepatic stellate, hepatic sinusoidal endothelial). (A-B) Gene expression analysis by RT-qPCR at day 28 of differentiation of von Willebrand factor (vW), VE-cadherin (Ve-cad), Tie2, Flk1, Lyve1, Stab1; desmin, activated leukocyte cell adhesion molecule (Alcam), and glial fibrillar), acidic protein (Gfap). Results are shown as fold change compared to undifferentiated cells at day 0.
Figure 3B:
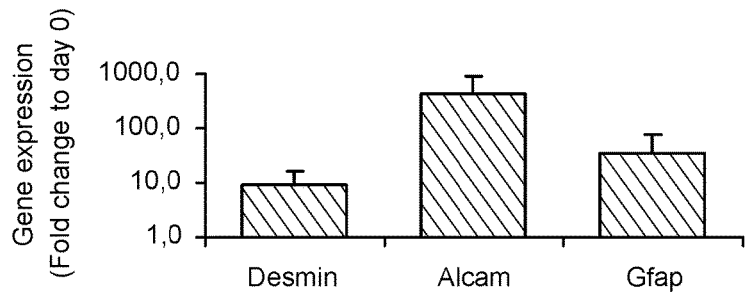

Gene expression was analyzed in three independently iPS cell lines. FIGS. 1 and 2 show the increase/decrease in expression of different genes for the J3 line as a fold change to undifferentiated cells (FIG. 1B-C), whereas results for J3, J23 and A1 as delta Ct change are shown in FIGS. 12-14. Stimulation of iPS cells with Activin-A and Wnt3a induced a transient expression of PS genes such as Brachyury, Mix11, Eomes and Goosecoid from day 2 to day 6 and by day 6 expression of genes expressed in ME and DE, such as Sox17, Cxcr4 and FoxA2 (Yasunaga et al., *Nat Biotechnol* 23:1542-50 (2005); Lowe et al., *Development* 128:1831-43 (2001)). (FIG. 1B and FIG. 1C). However, an increase in transcript levels for Sox7, which is expressed in primitive endoderm but not in PS/ME/DE (Seguin et al., *Cell Stem Cell August* 3:182-95 (2008), was also detected on day 6, suggesting that some cells may be undergoing differentiation to extraembryonic endoderm (FIG. 1C). Consistent with this, transcript levels for Hnf4a, Afp and Transthyretin (Ttr) were also induced by day 6 (FIG. 2A). Nevertheless, the greatest increase in Sox7, Afp and Ttr mRNA levels was seen between d6 and d28, suggesting differentiation to mesodermal cell lineage (Sox7) and hepatoblasts (Afp and Ttr) (FIG. 2A and FIG. 1-3). Other hepatoblast genes such as Hnf4α, and Krt19 started to be expressed between day 6 and day 10, in response to stimulation with BMP4 and bFGF, and genes expressed later in the liver development like Alb, or alpha-1 antitrypsin (Aat) were observed from day 14 onwards when cells were exposed to different FGFs (FIGS. 2A and B). Mature hepatocytes genes such as tyrosine amino-transferase (Tat), glucose-6-phosphate (G6p), Pepck and cytochromes were only induced during the maturation step, when cells were treated with HGF and follistatin (FIG. 2B).

As shown in FIGS. 12-14, the expression level for most of the genes is similar among the three lines examined.

To confirm the expression of key genes, immunocytochemistry for proteins expressed in PS/ME/DE cells and in hepatoblasts/hepatocytes was performed. At day 6, most cells expressed Sox17, and Mix11. Foxa2 was expressed in 70% of differentiating cells, indicating that a large percentage of cells undergo differentiation towards definitive endoderm in the first six days of differentiation. This is supported by the fact that Sox7, typical for extraembryonic endoderm, was only minimally upregulated on day 6 of differentiation (FIGS. 1C and 12-14). Moreover, less than 5% of the cells remained Oct4 positive. The immunohistological studies confirm the gene expression pattern of the day 28—differentiated progeny described above. Hnf4α, a key transcription factor involved in liver development and function, was expressed in about 30% of the total cells. To investigate the maturation state of liver committed cells staining for Afp, Krt19, Krt18 and Alb was performed. Krt19 and Afp are considered markers of bipotential hepatoblasts with capacity to differentiate to hepatocytes and cholangiocytes. Krt19 is lost when hepatoblasts differentiate towards hepatocytes, but maintained when they differentiate to cholangiocytes. Afp will remain expressed in immature hepatocytes but will be lost upon differentiation to cholangiocytes or mature hepatocytes (Stosiek et al., *Liver* 10:59-63 (1990); Lemaigre et al., *Curr Opin Genet Dev* 14:582-90 (2004)). Around 30% of iPSC progeny was Afp$^+$. Three populations of cells could be observed; a main population of Afp$^+$ cells that did not double label with Krt19, which may represent immature hepatocytes, a small population of Afp+/Krt19+ double positive cells, which would be consistent with hepatoblasts, and a small population of Krt19$^+$/Afp$^-$ cells which could be consistent with the generation of cholangiocytes. Colonies of albumin-bright positive polygonal cells can be observed and most Alb$^+$ cells double labeled with anti Krt18 antibodies, a keratin typically expressed in mature hepatocytes. Large plates of Alb$^-$/Afp$^+$ cells can be observed close to areas where Alb+/Afp+ are present. Moreover, one percent of the cells are Alb$^+$/Afp$^-$, suggesting that a fraction of Alb$^+$ cells have already lost the expression of Afp. Some albumin positive cells were binucleated. To investigate if differentiated cells had proliferative potential, double staining for Alb or Afp with Ki67 antibody was performed. Double positive Afp$^+$-Ki67$^+$ cells were present at day 28 of differentiation. However, no Alb positive cells expressed Ki67, suggesting that more immature hepatoblast-like cells could still have proliferative potential upon differentiation. Pepck starts to be expressed in the perinatal period and is a key gene regulating gluconeogenesis in hepatocytes. Some differentiated cells stained positive for Pepck. On day 28 of differentiation only sporadic colonies of Oct4 positive cells could be detected, indicating that a very small number of undifferentiated cells are present in the culture. Isotype control antibodies showed no positive staining Non-Hepatocyte Cells The hepatocyte differentiation protocol generated markers of nonparenchymal cells of the liver. It is well known that mesodermal cells are crucial for the in vivo generation of hepatic endoderm, and were also derived from the mesendodermal intermediary cells generated from iPS cells during the initial 6 days of differentiation. Different mesodermal cell types were co-generated during the differentiation process to hepatocytes. RT-qPCR demonstrated an upregulation of genes typically expressed in endothelial cells such as von Willebrand factor, VE-cadherin, Tie2 or Flk1 (FIG. 3A) (Nonaka et al., *Dev Dyn* 236:2258-67 (2007); Hansen et al., *Exp Cell Res* 303:160-73 (2005)), as well as genes expressed relatively specifically in liver sinusoidal endothelial cells like Lyve1 and Stab1 (FIG. 3A) (Nonaka et al., *Dev Dyn* 236:2258-67 (2007); Hansen et al., *Exp Cell Res* 303:160-73 (2005)). Moreover, genes expressed in hepatic stellate cells such as desmin, Gfap, and Alcam were expressed in differentiated progeny (Asahina et al., *Hepatology* 49:998-1011 (2009)). Cells double positive for Gfap and desmin are commonly thought to represent stellate cells in the mouse liver. d28 iPS cell progeny were assessed for co-expression of desmin and Gfap. A population of cells co-expresses both proteins. This protocol generates, aside from hepatocyte-like cells, also mesodermal cells that express genes and proteins of liver endothelial cells and stellate cells.

Functional Characterization of iPS Differentiated Progeny

Hepatocytes exert a number of synthetic, storage and detoxification functions, and these should also be present in stem cell derived progeny. Albumin secretion could be detected at day 14. Alb transcripts could also be detected at this time by RT-qPCR. Albumin production reached the maximum level on day 28. Minimal levels of glycogen could be detected in undifferentiated cells; however, glycogen content increased significantly upon hepatocyte differentiation. Urea production was detectable at day 28 of differentiation. Day 28 progeny acquired cytochrome Cyp1a2 activity. Cytochrome activity was inducible. When cells were maintained in the final maturation medium until day 42 of differentiation, basal levels of cytochrome activity did not increase, but phenobarbital induced a 45% increase of Cyp1a2 activity. These data indicate that iPS-derived hepatocyte-like cells exert functional characteristics of hepatocytes.

The data demonstrate that mouse iPS can be directed to differentiate to hepatocyte-like cells by mimicking embryonic and fetal liver development. iPS cells are specified to PS/ME/DE followed by the expression of hepatoblast and finally more mature hepatocyte genes, proteins as well as functions. Most differentiated cells co-express Afp and Alb suggesting an incomplete cell maturation, which is also typically found in differentiation cultures of mouse and human embryonic stem cells. iPS derived hepatocyte-like cells exert synthetic, storage and detoxifying properties, indicating that functional hepatocyte-like cells are generated.

Example 2

Expression of (hepatic sinusoidal) endothelial genes is found maximally at d20. Human ESC were cultured sequentially with Activin A/Wnt3a, BMP4/FGF2, FGF1, 4 and 8, and HGF/Follistatin, in 2% serum on matrigel coated plates for 28 days. On d0, 6, 10, 14, 20 and 28, cells were harvested and transcripts found in healthy liver-derived of activated hepatic sinusoidal endothelial cells (HSEC) quantified using RT-qPCR. The results show that there is maximal up-regulation of HSEC genes on day 20 of differentiation. See FIG. 4.

Expression of hepatic stellate genes (quiescent and some non-quiescent) is found maximally at d20. Human ESC were cultured sequentially with Activin A/Wnt3a, BMP4/FGF2, FGF1, 4 and 8, and HGF/Follistatin, in 2% serum on matrigel coated plates for 28 days. On d0, 6, 10, 14, 20 and 28, cells were harvested and transcripts found in quiescent and activated hepatic stellate cells (HSC) (see table) quantified using RT-qPCR. The results show that there is maximal up-regulation of stellate cell genes on day 20 of differentiation (shown in graph) (average of n=2/3). See FIG. 5.

Figure 6:
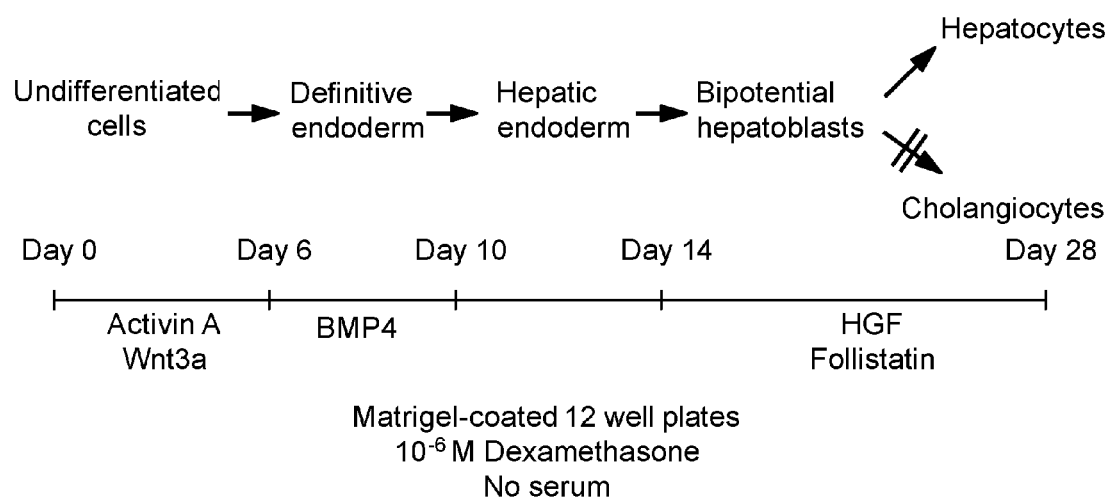
FIG. 6. Modified differentiation protocol. This figure outlines an alternative differentiation protocol for producing cells with a hepatocyte phenotype as well as cells with a hepatic stellate phenotype and cells with a hepatic sinusoidal endothelial phenotype.

New differentiation protocol. This figure outlines an alternative differentiation protocol for producing cells with a hepatocyte phenotype as well as cells with a hepatic stellate phenotype and cells with a hepatic sinusoidal endothelial phenotype. See FIG. 6.

Figure 7:
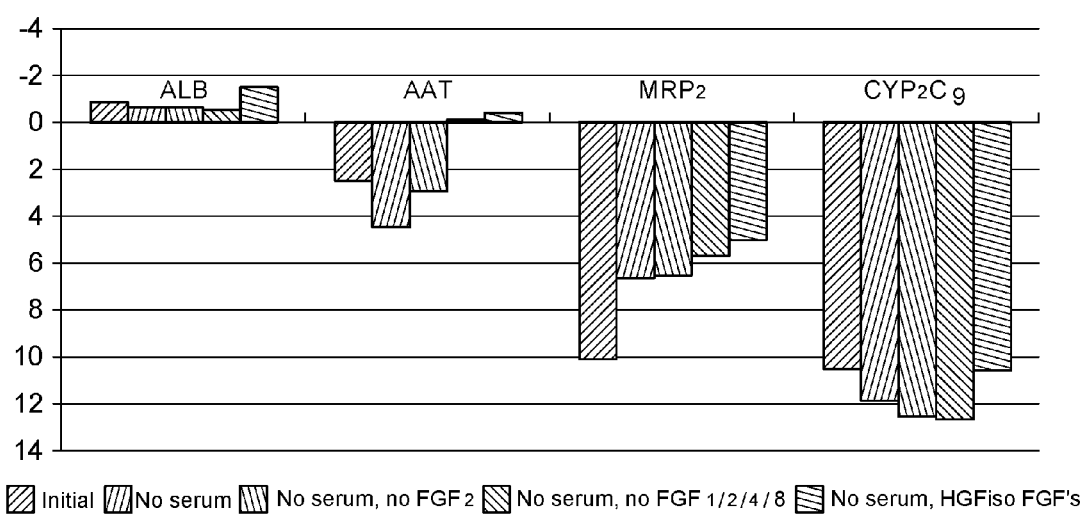
FIG. 7. Increased expression of AAT and MRP$_2$ when differentiation is done without serum, and without addition of FGF 1, 2, 4 and 8, or when FGF 1, 4 and 8 is replaced by HGF. Human ESC were cultured sequentially with Activin A/Wnt3a, BMP4 and HGF/Follistatin in serum-free medium with or without FGF2 in step 2, FGF1/4/8 in step 3, or with HGF starting from d14. Expression of ALB, AAT, Cyp2C9 and MRP2 mRNA was assessed by RT-qPCR on day 28. Results are shown for the expression of these genes in serum-containing or -free conditions.

Increased expression of AAT and $MRP_2$ when differentiation is done with serum, and without addition of $FGF_{1, 2, 4}$ and 8, or when $FGF_{1,4}$ and 8 replaced by HGF. Human ESC were cultured sequentially with Activin A/Wnt3a, BMP4 and HGF/Follistatin in serum-free medium with or without also FGF2 in step2, FGF1/4/8 in step 3, or with HGF starting from d14. Expression of ALB, AAT, Cyp2C9 and MRP2 mRNA was assessed by RT-qPCR on day 28. Results are shown for the expression of these genes in serum-containing or —free conditions. See FIG. 7.

Figure 8:
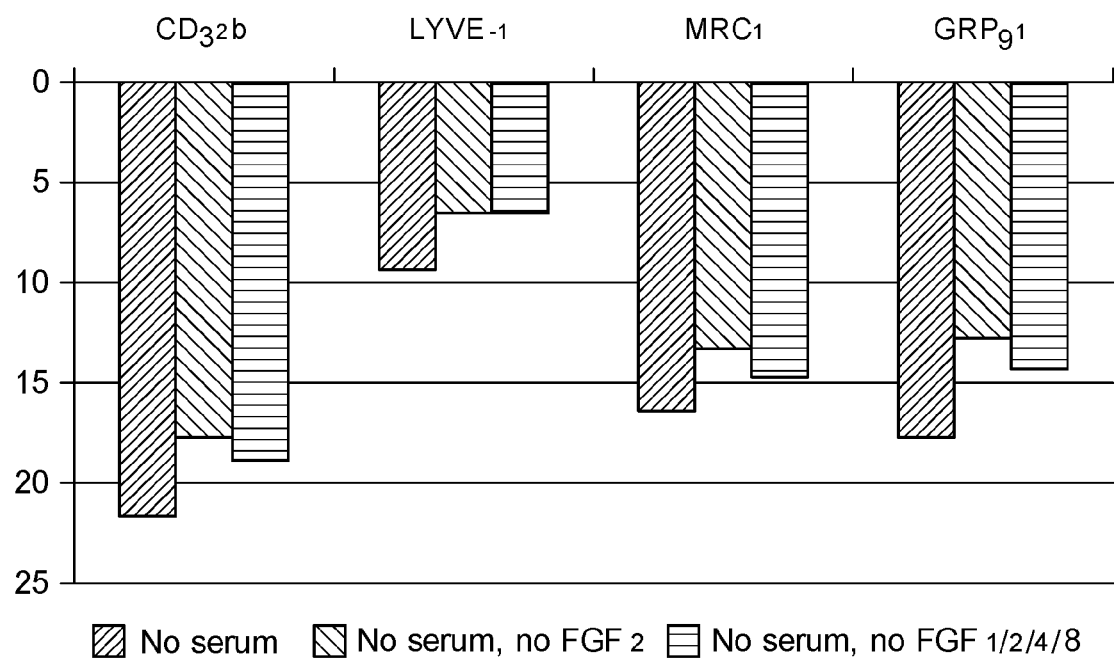
FIG. 8. Removal of serum and FGF1, 2, 4 and 8 has a positive effect on the generation of stellate and endothelial cells. Human ESC were cultured sequentially with Activin A/Wnt3a, BMP4/FGF2, FGF1, 4 and 8, and HGF/Follistatin in serum free medium vs. 2% FCS. Expression of CD32b, LYVE-1, MRC1, and GRP91 mRNA was assessed by RT-qPCR on day 28. Results are shown for the expression of these genes in serum-free conditions+/−FGFs.

Removal of serum and $FGF^{1, 2, 4}$ and 8 has also positive effect on generation of stellate and endothelial cells. Human ESC were cultured sequentially with Activin A/Wnt3a, BMP4/FGF2, FGF1, 4 and 8, and HGF/Follistatin in serum free medium vs. 2% FCS. Expression of CD32b, LYVE-1, MRC1, and GRP91 mRNA was assessed by RT-qPCR on day 28. Results are shown for the expression of these genes in serum-free conditions+/−FGFs. See FIG. 8.

Figure 9A:
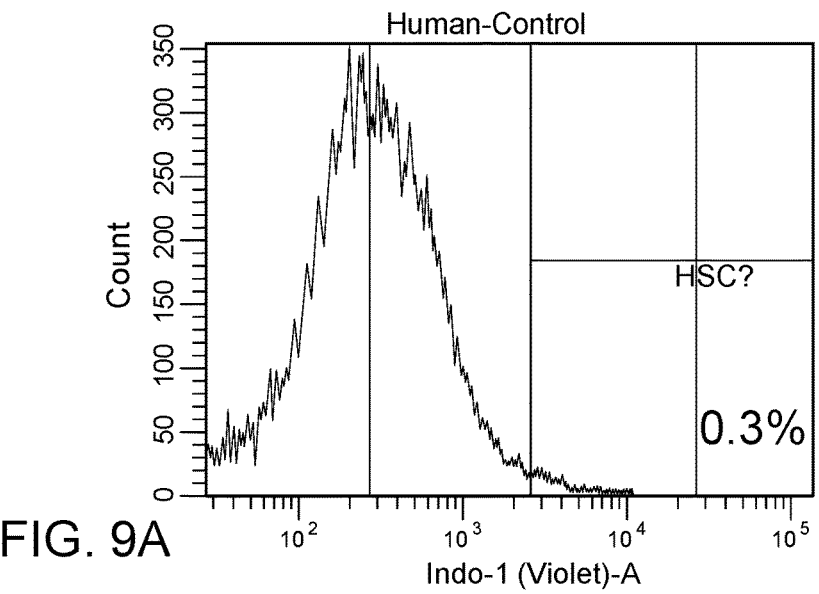
FIGS. 9A-9C. Isolation of stellate cells from hESC progeny. Human ESC were cultured sequentially with Activin A/Wnt3a, BMP4, FGF1, 4, and 8, and HGF/Follistatin, in serum-free medium on matrigel coated plates for 20 days. Human ESC were treated with vitamin A, that then is stored in stellate cells under the form of retinyl esters in lipid droplets. This gives the cells a fluorescent phenotype under UV Laser. Fluorescent cells were selected from the ESC/-iPSC progeny (frequency ranging between 3 and 5%), RNA was extracted from the Indo-1 (Violet)—A positive and negative fraction and analyzed for hepatic stellate cell gene expression (C). As can be seen from the figure (A-B), a number of stellate (activated and quiescent) genes were significantly enriched in the Indo-1 (Violet)—A positive fraction. The method for isolation was according to Geerts et al., *Hepatology* 27:590-598 (1998).
Figure 9B:
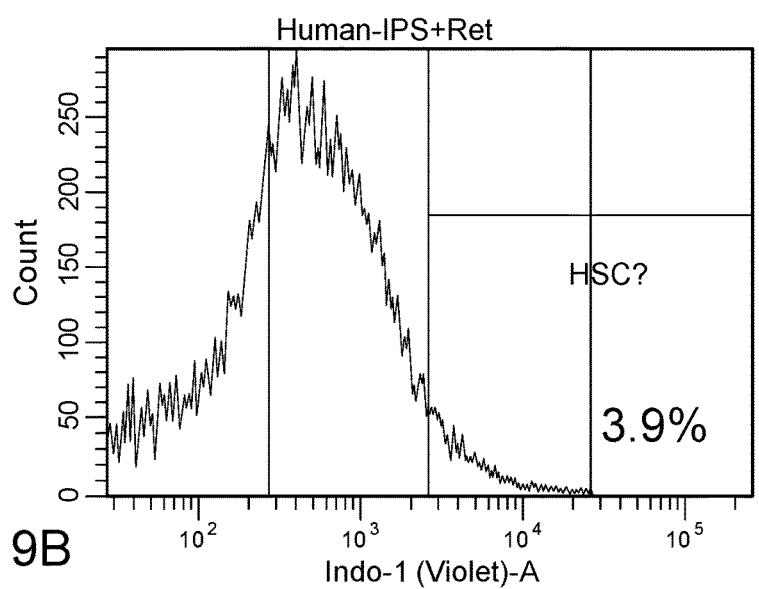
Figure 9C:
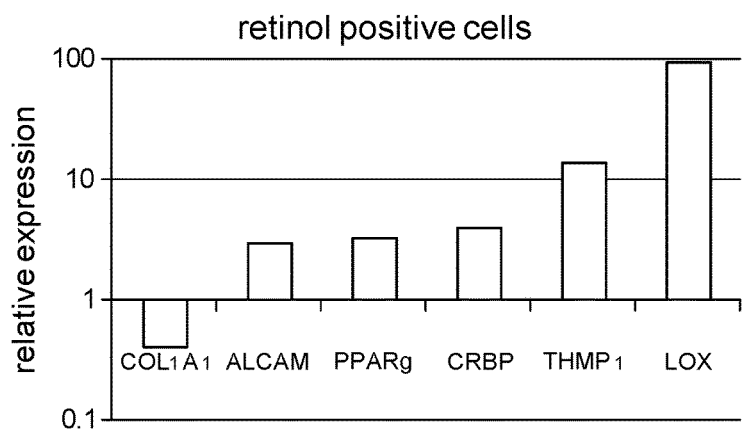

Isolation of stellate cells from hESC progeny. Human ESC were cultured sequentially with Activin A/Wnt3a, BMP4, FGF1, 4, and 8, and HGF/Follistatin, in serum-free medium on matrigel coated plates for 20 days. Human ESC were treated with vitamin A, that then is stored in stellate cells under the form of retinyl esters in lipid droplets. This gives the cells a fluorescent phenotype under UV Laser. Fluorescent cells were selected from the ESC/−iPSC progeny (frequency ranging between 3 and 5%), RNA was extracted from the Indo-1 (Violet)—A positive and negative fraction and analyzed for hepatic stellate cell gene expression. As can be seen from FIG. 9, a number of stellate (activated and quiescent) genes were significantly enriched in the Indo-1 (Violet)—A positive fraction. The function of the cells has not yet been evaluated. The method for isolation was according to Geerts et al., *Hepatology* 27:590-598 (1998). See FIG. 9.

Figure 10A:
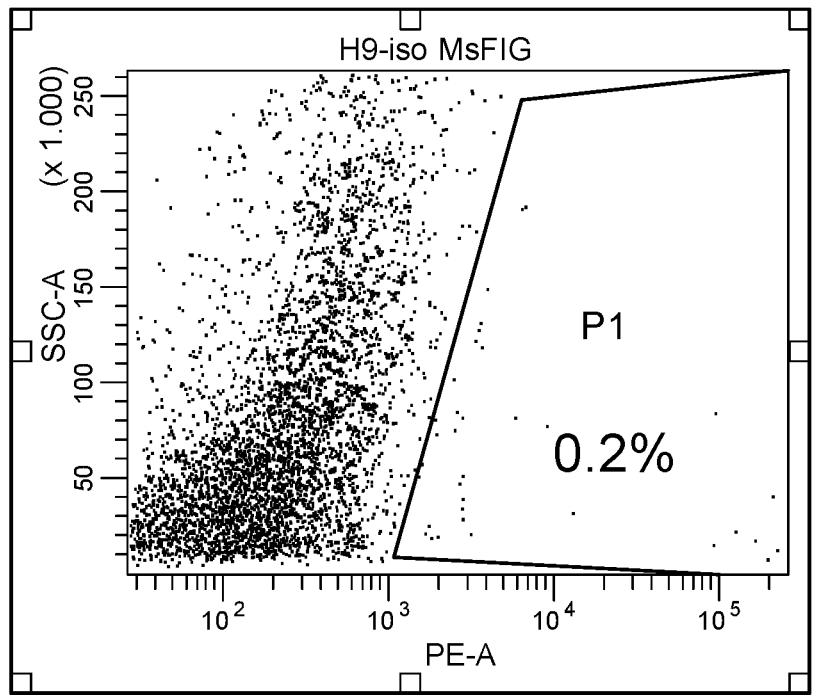
FIGS. 10A and 10B. Endothelial cell isolation from mixed ESC/iPSC cultures using VE-cadherin antibody. Human ESC were cultured sequentially with Activin A/Wnt3a, BMP4, FGF1, 4, and 8, and HGF/Follistatin, in serum-free medium on matrigel coated plates for 20 days, per the protocol in FIG. 11. On day 20, cells were isolated using 0.05% trypsin, and stained with antibodies against VE-cadherin, or isotype control antibody, and isolated from the mixed population by FACS (A-B).
Figure 10B:
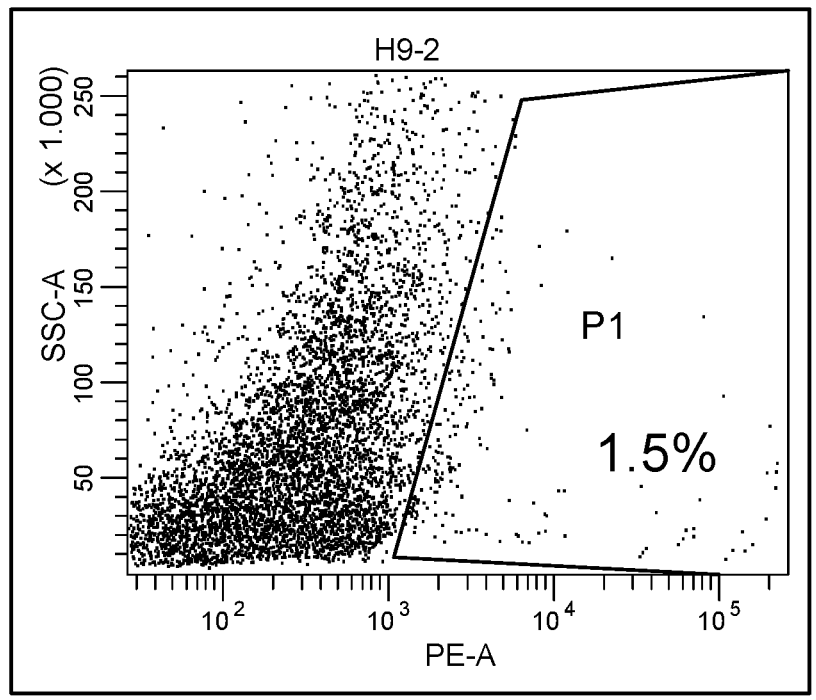

Endothelial cell isolation from mixed ESC/iPSC cultures using VE-cadherin antibody. Human ESC were cultured sequentially with Activin A/Wnt3a, BMP4, FGF1,4 and 8, and HGF/Follistatin, in serum-free medium on matrigel coated plates for 20 days, per the protocol in FIG. 7. On day 20, cells were isolated using 0.05% trypsin, and stained with antibodies against VE-cadherin (lower panel), or isotype control antibody (upper panel), and isolated from the mixed population by FACS. See FIG. 10.

Figure 11:
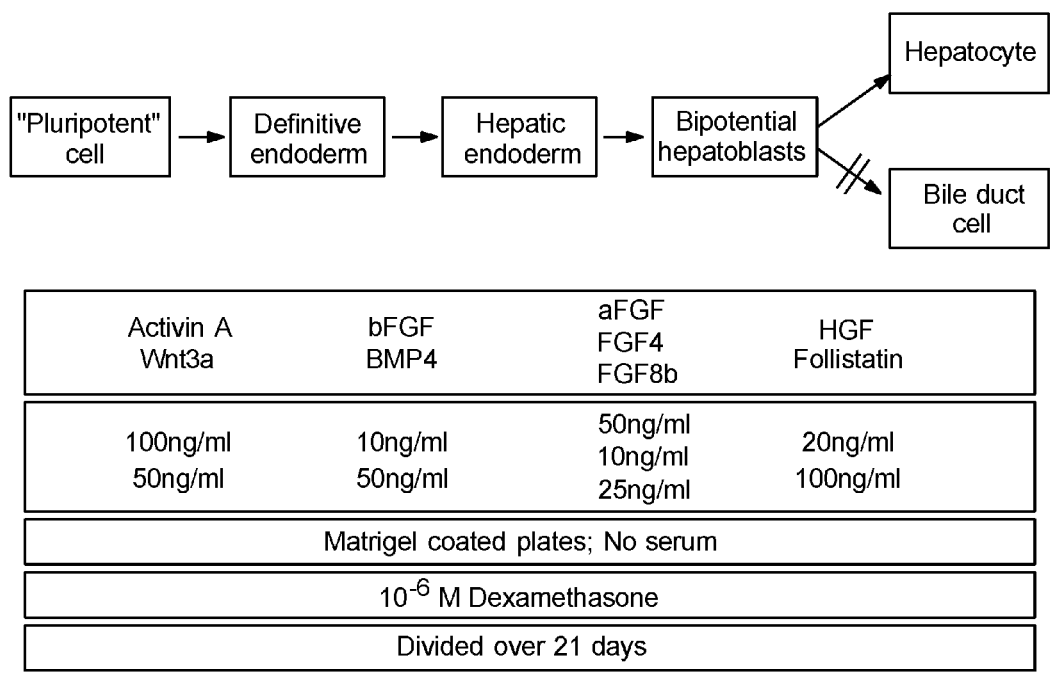
FIG. 11 provides a 4-step in vitro differentiation protocol. Days 0-6: Activin A (100 ng/ml) and Wnt3a (50 ng/ml). Days 6-10: bFGF (10 ng/ml) and BMP4 (50 ng/ml). Days 10-14: aFGF (50 ng/ml), FGF4 (10 ng/ml) and FGF8b (25 ng/ml). Days 14-21: HGF (20 ng/ml) and Follistatin (100 ng/ml).
Figure 12A:
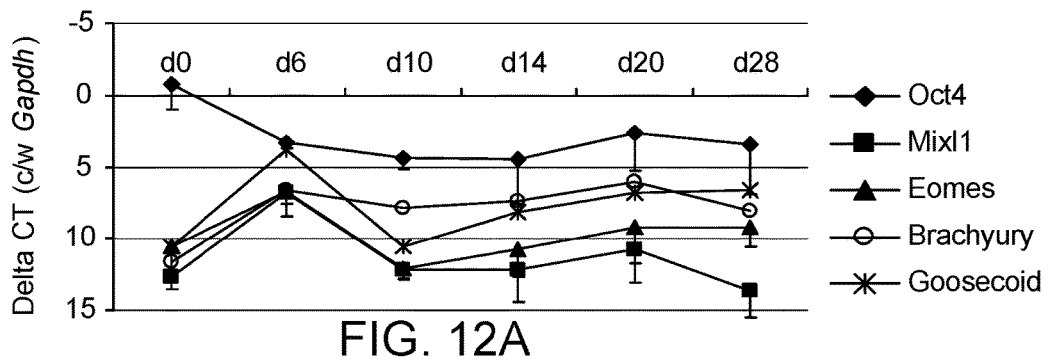
FIGS. 12A-12D. Gene expression analysis at different steps of the differentiation. Gene expression analysis by real-time RT-PCR at day (d) d0, d6, d10, d14, d20, and d28 of the differentiation of the iPS cell line J3. Key genes expressed in (A and B) primitive streak/mesendoderm/definitive endoderm, (C) hepatoblasts and immature hepatocytes and (D) mature hepatocytes are analyzed. Results are shown as mean delta Ct value with respect to Gapdh±standard deviation of three independent differentiations.
Figure 12B:
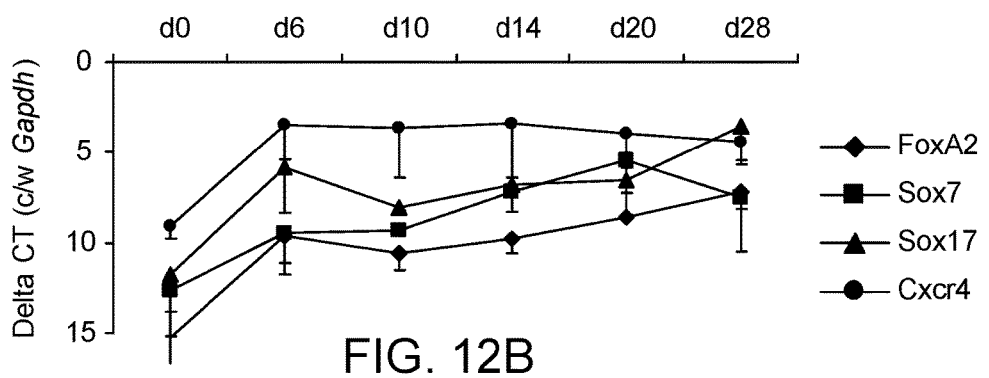
Figure 12C:
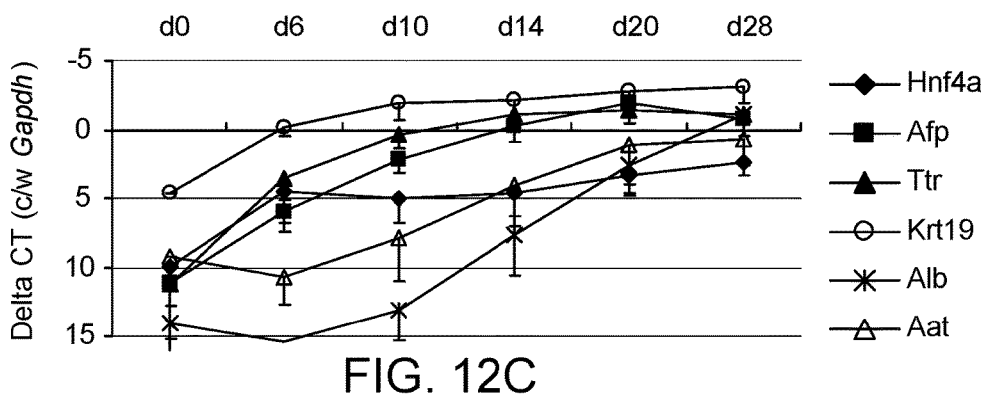
Figure 12D:
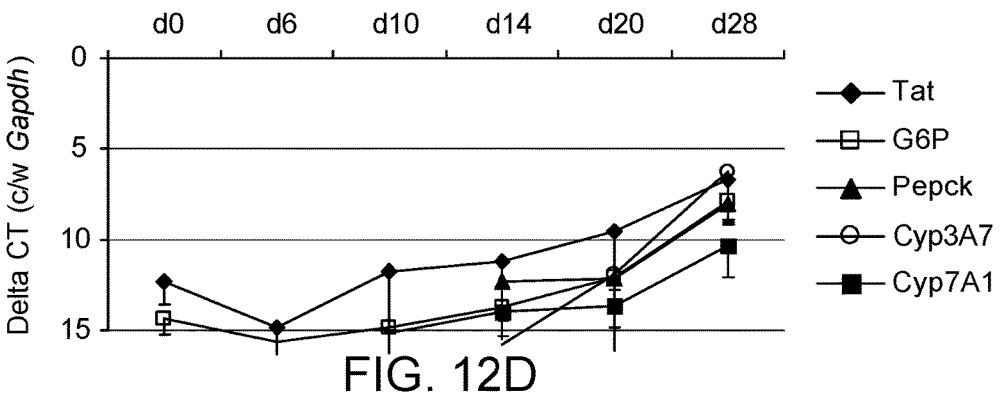
Figure 13A:
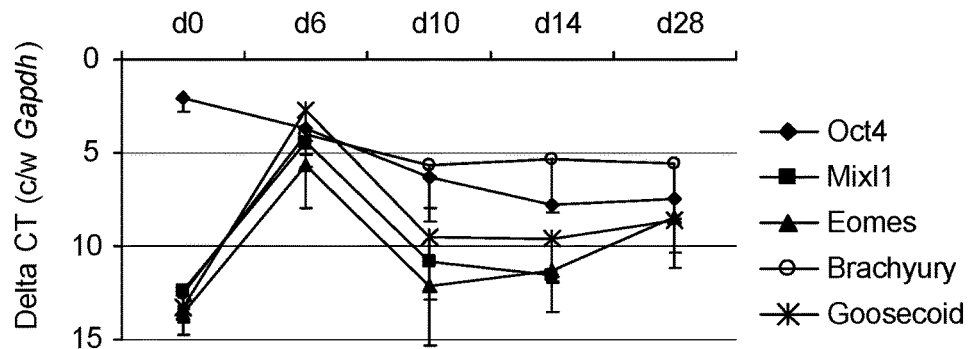
FIGS. 13A-13D. Gene expression analysis at different steps of the differentiation. Gene expression analysis by real-time RT-PCR at day (d) d0, d6, d10, d14, and d28 of the differentiation of the iPS cell line J23. Key genes expressed in (A and B) primitive streak/mesendoderm/definitive endoderm, (C) hepatoblasts and immature hepatocytes, and (D) mature hepatocytes are analyzed. Results are shown as mean delta Ct value with respect to Gapdh±standard deviation of three independent differentiations.
Figure 13B:
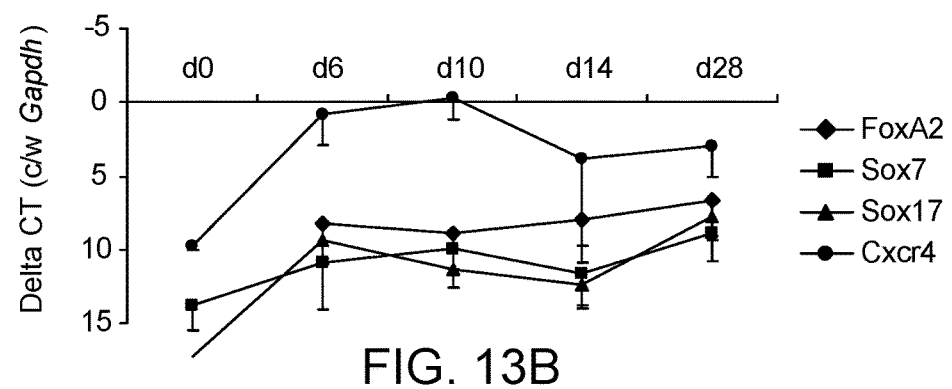
Figure 13C:
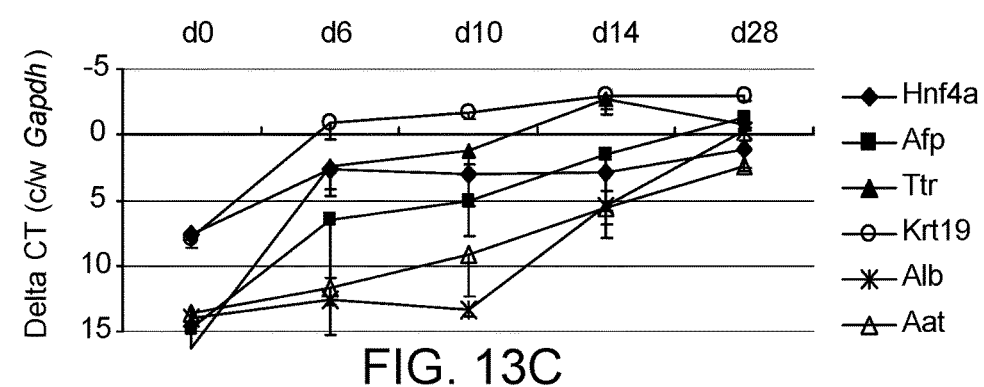
Figure 13D:
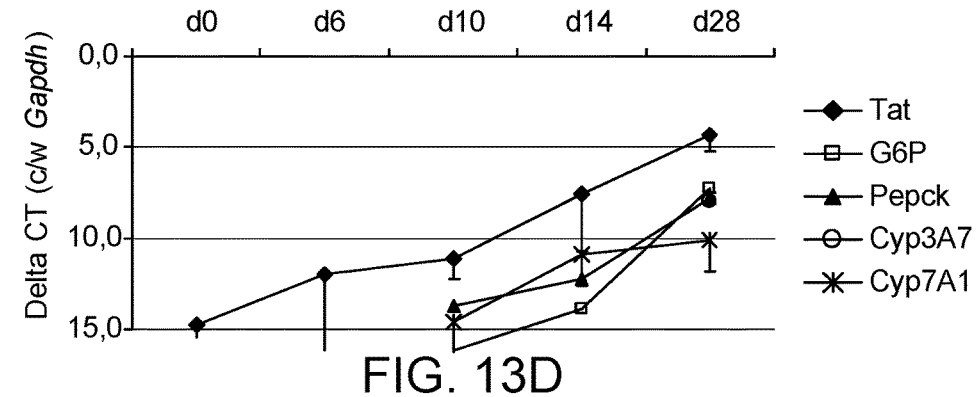
Figure 14A:
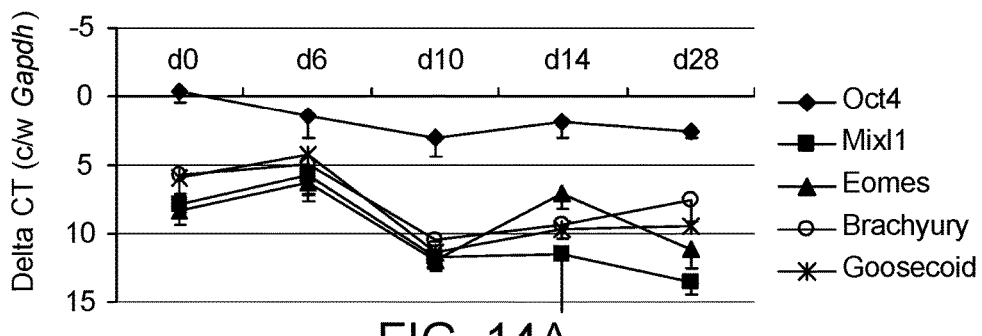
FIGS. 14A-14D. Gene expression analysis at different steps of the differentiation. Gene expression analysis by real-time RT-PCR at day (d) d0, d6, d10, d14, and d28 of the differentiation of the iPS cell line A1. Key genes expressed in (A and B) primitive streak/mesendoderm/definitive endoderm, (C) hepatoblasts and immature hepatocytes and (D) mature hepatocytes are analyzed. Results are shown as mean delta Ct value with respect to Gapdh±standard deviation of three independent differentiations.
Figure 14B:
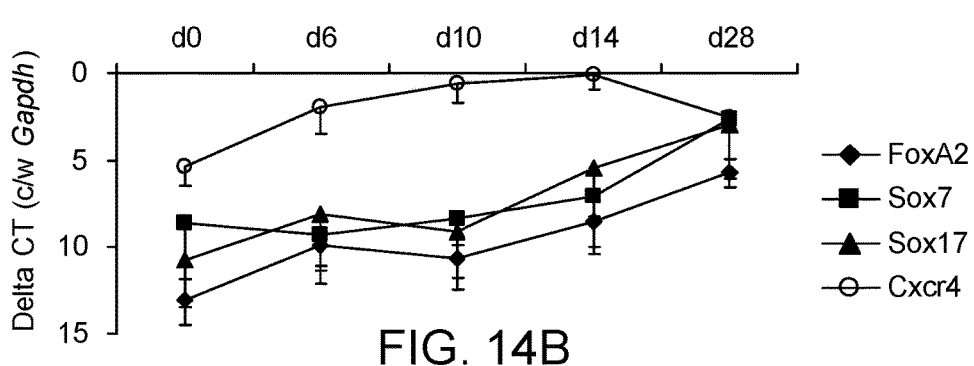
Figure 14C:
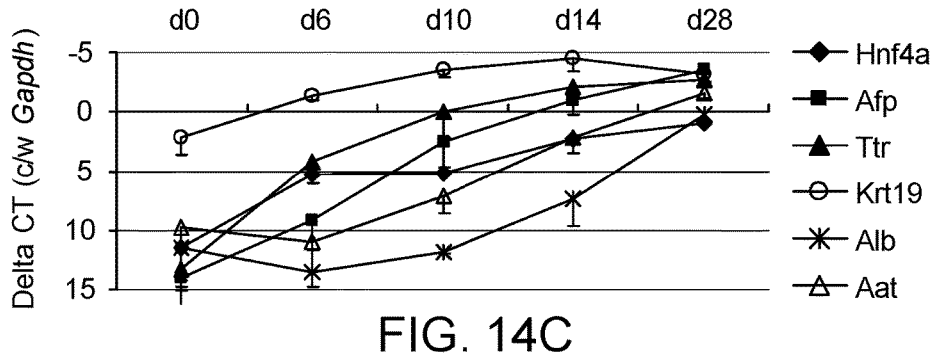
Figure 14D:
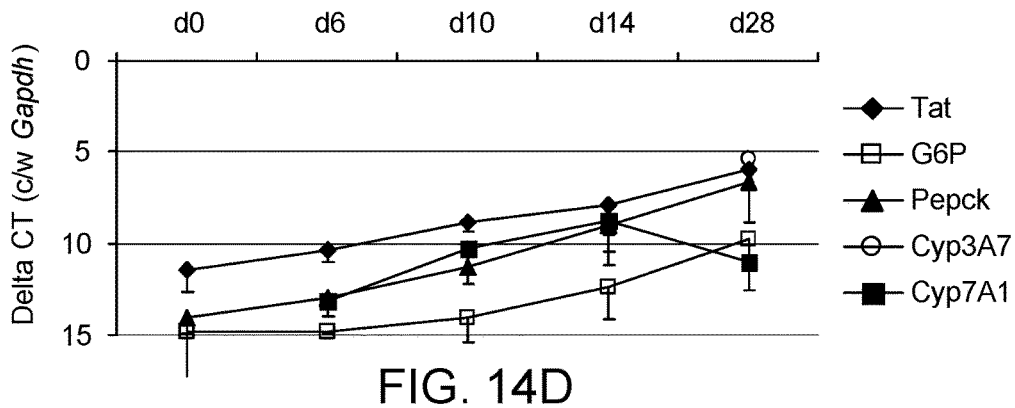

FIG. 11 provides a 4-step in vitro differentiation protocol. Days 0-6: Activin A (100 ng/ml) and Wnt3a (50 ng/ml).

Days 6-10: bFGF (10 ng/ml) and BMP4 (50 ng/ml). Days 10-14: aFGF (50 ng/ml), FGF4 (10 ng/ml) and FGF8b (25 ng/ml). Days 14-21: HGF (20 ng/ml) and Follistatin (100 ng/ml).

Example 3

As an alternative to the VE-cadherin sorting, endothelial cells were isolated from hESC differentiations (using the four-step differentiation protocol, i.e., with the FGFs) by FACS with a Tie2 antibody or a combination of Tie2 and CD31 antibodies. The sorted endothelial cells were analyzed by qRT-PCR on day 14 or day 20 of the differentiation process. On day 14, ~5% of the differentiated cultures expressed Tie2. On day 20, ~25% of the differentiated cultures expressed Tie2 and ~1% co-expressed Tie2 and CD31. Expression of LSEC marker CD32b was upregulated in time in the Tie2 fraction. Compared to the Tie2 fraction, CD32b and Stab1 expression was higher in the Tie2+CD31+ fraction at day 20 of differentiation.

The invention claimed is:
1. A method for producing cells with a hepatic stellate phenotype and cells with a hepatic sinusoidal endothelial phenotype, comprising:
  (a) culturing pluripotent cells with about 5 ng/ml to about 500 ng/ml Wnt3a and about 10 ng/ml to about 1,000 ng/ml ActivinA;
  (b) then culturing the cells of step (a) with about 1 ng/ml to about 100 ng/ml bFGF and about 5 ng/ml to about 500 ng/ml BMP4;
  (c) then culturing the cells of step (b) with about 5 ng/ml to about 500 ng/ml aFGF, about 1 ng/ml to about 100 ng/ml FGF4 and about 2.5 ng/ml to about 250 ng/ml FGF8b;
  (d) then culturing the cells of step (c) with about 2 ng/ml to about 200 ng/ml HGF and about 10 ng/ml to about 1,000 ng/ml Follistatin; and
  (e) isolating hepatic stellate cells and/or hepatic endothelial sinusoidal cells produced by the differentiation protocol, wherein the pluripotent cells are non-embryonic germ cells, embryonic stem cells, or germ cells and can differentiate into at least one cell type of at least two of the endodermal, ectodermal, and mesodermal embryonic lineages and/or express oct4 or telomerase.
2. The method of claim 1, wherein the pluripotent cells express telomerase.
3. The method of claim 1, wherein the pluripotent cells express oct4.
4. The method of claim 1, wherein the pluripotent cells can differentiate into at least one cell type of at least two of the endodermal, ectodermal, and mesodermal embryonic lineages.
5. The method of claim 1, wherein the pluripotent cells express telomerase and can differentiate into at least one cell type of at least two of the endodermal, ectodermal, and mesodermal embryonic lineages.
6. The method of claim 1, wherein the pluripotent cells express oct4 and can differentiate into at least one cell type of at least two of the endodermal, ectodermal, and mesodermal embryonic lineages.
7. The method of any of claims 1 and 2-6, wherein the cells that are contacted with Wnt3a and ActivinA are human bone marrow-derived cells.
8. The method of claim 1 where isolation of hepatic stellate cells in step (e) is carried out by one or more markers selected from the group consisting of Vitamin A$^+$, PPARg$^+$, GFAP$^+$, GPR91$^+$, ALCAM, CRBP$^{high}$, p75NTR$^+$, COL1a1$^{high}$, and TIMP-1$^{low}$.
9. The method of claim 1 where isolation of liver sinusoidal endothelial cells in step (e) is carried out using one or more markers selected from the group consisting of CD32b$^+$, Stab-1$^+$, Stab-2$^+$, L-SIGN$^+$, and MRC1$^+$.
10. A method for producing cells with a hepatic stellate phenotype and cells with a hepatic sinusoidal endothelial phenotype, comprising:
  (a) culturing pluripotent cells with about 50 ng/ml Wnt3a and about 100 ng/ml ActivinA;
  (b) then culturing the cells of step (a) with about 10 ng/ml bFGF and about 50 ng/ml BMP4;
  (c) then culturing the cells of step (b) with about 50 ng/ml aFGF, about 10 ng/ml FGF4 and about 25 ng/ml FGF8b;
  (d) then culturing the cells of step (c) with about 20 ng/ml HGF and about 100 ng/ml Follistatin; and
  (e) isolating hepatic stellate cells and/or hepatic endothelial sinusoidal cells produced by the differentiation protocol, wherein the pluripotent cells express telomerase, oct4, and can differentiate into at least one cell type of at least two of the endodermal, ectodermal, and mesodermal embryonic lineages and are derived from human bone marrow.

* * * * *